US008431051B2

(12) United States Patent
Miteva et al.

(10) Patent No.: US 8,431,051 B2
(45) Date of Patent: *Apr. 30, 2013

(54) ORGANIC POLYMERIC PHOTON UP-CONVERSION NANOPARTICLES FOR BIOLOGICAL APPLICATIONS

(75) Inventors: Tzenka Miteva, Stuttgart (DE); Gerde Fuhrmann, Stuttgart (DE); Gabriele Nelles, Stuttgart (DE); Vladimir Yakutkin, Stuttgart (DE); Slanislav Balouchev, Mainz (DE)

(73) Assignee: Sony Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/791,334

(22) Filed: Jun. 1, 2010

(65) Prior Publication Data
US 2010/0330026 A1 Dec. 30, 2010

(30) Foreign Application Priority Data

May 29, 2009 (EP) .................................. 09007219

(51) Int. Cl.
*F21V 9/00* (2006.01)
*G02B 5/02* (2006.01)
*G02C 7/10* (2006.01)
*G02F 1/361* (2006.01)
*G03B 11/00* (2006.01)
*C08L 53/00* (2006.01)
*C09J 7/02* (2006.01)

(52) U.S. Cl.
USPC ......... 252/582; 424/78.18; 524/505; 977/773

(58) Field of Classification Search ................ 252/582, 252/21; 359/326; 435/6; 424/78.18; 524/505; 540/145; 977/773
See application file for complete search history.

(56) References Cited

U.S. PATENT DOCUMENTS

| 2005/0056815 | A1* | 3/2005 | Miteva et al. | 252/582 |
| 2009/0224659 | A1 | 9/2009 | Miteva et al. | |
| 2009/0251765 | A1 | 10/2009 | Miteva et al. | |
| 2009/0290211 | A1* | 11/2009 | Miteva et al. | 359/326 |
| 2010/0301285 | A1* | 12/2010 | Miteva et al. | 252/582 |

FOREIGN PATENT DOCUMENTS

WO WO2009061406 A1 * 5/2009

OTHER PUBLICATIONS

U.S. Appl. No. 12/791,237, filed Jun. 1, 2010, Miteva, et al.
U.S. Appl. No. 12/746,273, filed Jun. 4, 2010, Miteva, et al.

* cited by examiner

*Primary Examiner* — Bijan Ahvazi
(74) *Attorney, Agent, or Firm* — Oblon, Spivak, McClelland, Maier & Neustadt, L.L.P.

(57) ABSTRACT

The present invention relates to organic polymeric photon up-conversion nanoparticles for biological applications, such as labeling and/or detection of cells, biological (macro-) molecules or other analytes, as well as for sensing temperature, pressure, oxygen and other substances that influence the up-conversion process. It further relates to organic photon up-conversion nanoparticles for singlet oxygen generation and the treatment of diseases, such as cancer.

14 Claims, 14 Drawing Sheets

ORGANIC POLYMERIC PHOTON UP-CONVERSION NANOPARTICLES FOR BIOLOGICAL APPLICATIONS

The present invention relates to organic polymeric photon up-conversion nanoparticles for biological applications, such as labeling and/or detection of cells, biological (macro-) molecules or other analytes, as well as for sensing temperature, pressure, oxygen and other substances that influence the up-conversion process. It further relates to organic photon up-conversion nanoparticles for singlet oxygen generation and the treatment of diseases, such as cancer.

In a number of systems, it has been observed that irradiation by light with longer wavelength causes emission of a light with shorter wavelength. This phenomenon is referred to as "frequency up-conversion" or "photon up-conversion".

The use of photon up-conversion as a reporter system adds a powerful tool to modern detection technologies (Corstjens et al., 2005, *IEE Proc.-Nanobiotechnol.*, Vol. 152, No. 2, 64-72; Kuningas et al., 2005, *Analytical Chemistry*, Vol. 77, No. 22, 7348-55; Rantanen et al., 2008, *Angew. Chem. Int. Ed.*, 47, 3811-13; Rantanen et al., 2007, *Analytical Chemistry*, Vol. 79, No. 16, 6312-18; U.S. Pat. No. 6,399,397). In contrast to conventional fluorescent reporters, up-converting particles (UCPs) show almost no bleaching and allow permanent excitation with simultaneous signal integration. A large anti-Stokes shift (up to 500 nm) separates discrete emission peaks from the deep red infrared excitation source. Along with the unmatched contrast in biological specimens due to the absence of autofluorescence upon infrared excitation, up-converting technology (UPT) has unique properties for highly sensitive particle-based assays.

Existing photon up-conversion particles are either based on inorganic phosphors (Ungun et al., 2008, *Optics Express*, Vol. 17, No. 1, 80-86; Lim et al., 2005, *Nano Lett.*, Vol. 6, No. 2, 169-174) or on two-photon absorption (Gao et al., 2006, *Nano Lett.*, Vol. 6, No. 11, 2383-6), which results from the simultaneous absorption of two photons of identical or different frequencies by dyes with a large two-photon absorption (TPA) cross-section.

However, the inorganic based UCPs (and in general the UC systems as such) as well as the particles based on TPA work only with high intensity monochromatic laser light, normally in the order of $kW/cm^2$, and they require very high spectral power density of the excitation light source, typically in the order of $Wnm^{-1}$, additionally, they have low efficiencies which have so far only been reported for crystalline powders as ca. 1% to a maximum of 4% but these are only when for high intensities (Page et al., 1998, *J. Opt. Soc. Am. B*, Vol. 15, No. 3, 996). Furthermore, the systems reported so far only have emission characteristics which are intrinsic to the used corresponding materials, without any possibility to influence the ratio of emitted wavelengths. Due to their inorganic nature, the use of these systems in biological or medical applications is problematic. Currently known organic systems also require high excitation intensities in the $kW/cm^2$ range and often provide low versatility with respect to the absorption and/or emission characteristics.

Accordingly, it was an object of the present invention to provide organic nanoparticles for photon up-conversion, which are biocompatible and, thus, suitable for biological applications, such as probing and labelling of biological molecules, as well as for medical applications, such as photodynamic therapy. They should have surface functional groups suitable for standard bio-conjugations and be chemically stable in an aqueous environment. The up-conversion nanoparticles should further show a great versatility with respect to the radiation wavelengths involved, both incident and emitted, and may, therefore, be tailor-made depending on the desired excitation and/or emission characteristics. In addition, the nanoparticles should allow the efficient use of low intensity or low spectral density light sources.

The objects of the present invention are solved by a polymeric nanoparticle for use in biological applications comprising
a medium for photon up-conversion and a stabilizing agent, said medium comprising at least two components and a polymeric organic matrix component, said polymeric organic matrix component forming a polymeric matrix in which polymeric matrix said at least two components are distributed, wherein a first component of said at least two components is capable of absorbing light at a first wavelength region $w \leq \lambda_1 \leq x$, which first component acts as a sensitizer in said medium, and wherein a second component of said at least two components is capable of emitting light at a second wavelength region $y \leq \lambda_2 \leq z$, which second component acts as an emissive component in said medium, wherein $\lambda_2 \leq \lambda_1$, and wherein, upon absorption of light by said first component at said first wavelength region $w \leq \lambda_1 \leq x$, said emissive component emits light at said second wavelength region $y \leq \lambda_2 \leq z$, wherein said first component and said second component are organic compounds.

In one embodiment, said stabilizing agent is a polymer selected from hydrophilic polymers and amphiphilic polymers, said amphiphilic polymers having a hydrophobic part and a hydrophilic part, wherein said hydrophobic part also forms part of said polymeric matrix, wherein said amphiphilic polymer is selected from amphiphilic copolymers, hydrophobic polymers with a covalently attached hydrophilic part, hydrophilic polymers with a covalently attached hydrophobic part, and polyelectrolytes having a hydrophobic part.

In one embodiment said stabilizing agent is an amphiphilic copolymer, selected from amphiphilic block, graft, random and alternating copolymers, preferably an amphiphilic block copolymer or an amphiphilic graft copolymer.

In one embodiment said amphiphilic copolymer is an amphiphilic block copolymer comprising at least one hydrophobic block and at least one hydrophilic block.

In one embodiment said at least one hydrophobic block forms part of said polymeric matrix or is said polymeric matrix, and wherein said at least one hydrophilic block forms a hydrophilic shell surrounding said matrix. The hydrophilic shell confers stability to the nanoparticle in an aqueous environment and renders it water-soluble and biocompatible.

In one embodiment said hydrophilic polymer or said at least one hydrophilic block of said amphiphilic copolymer is selected from the group comprising: polyethylene glycols, polyethylene oxides, polyacrylamides, polyacrylic acids and their related polymers and copolymers, acrylates, maleic anhydride copolymers, methacrylate, ethacrylate and related polymers, amine-functional polymers, such as polyethyleneimines, poly-2-ethyl-2-oxazolines and polyallylamines, ethers, such as polymethylvinyl ethers, polyepoxysuccinic acid, glycerol propoxylates, styrenes, such as polystyrenesulfonate and related polymers, vinyl acids, and vinyl alcohols, such as polyvinyl alcohols, poly(vinylpyridines) and poly(vinylpyrrolidone), as well as copolymers and combinations thereof.

In one embodiment said at least one hydrophobic block of said amphiphilic block copolymer is selected from the group, but not limited to, comprising polystyrenes (including styrene copolymers as well as substituted and modified styrenes), styrene-butadiene copolymers, polystyrene-based elastomers, polyethylenes, polypropylenes, polytetrafluoroethylenes, extended polytetrafluoroethylenes, polyacrylates, polymethylmetacrylates, ethylene-co-vinyl acetates, polysiloxanes (e.g. polymethylsiloxanes, such as polydimethylsiloxane, polyphenylmethylsiloxanes, such as polyphenylmethylsiloxane, in general their copolymers as well as substituted and modified polysiloxanes), polyethers, polyurethanes, polyether-urethanes, polyethylene terephthalates, polysulphones.

In one embodiment said at least one hydrophilic block of said amphiphilic block copolymer carries a functional group allowing bioconjugation, i.e. the coupling of the nanoparticles to biological molecules, such as peptides, proteins, carbohydrates, lipids and nucleic acids, or the attachment of an additional dye that is excited by the light emitted by the up-conversion nanoparticles. The functional group can be attached along the polymer chain or as a terminal group.

In one embodiment said functional group is selected from the group comprising —COOH (carboxylate), —SH (thiol), —NH$_2$, —NHS, alkynyl groups, —N$_3$, aldehyde, ketone, biotin group, and a group having the formula

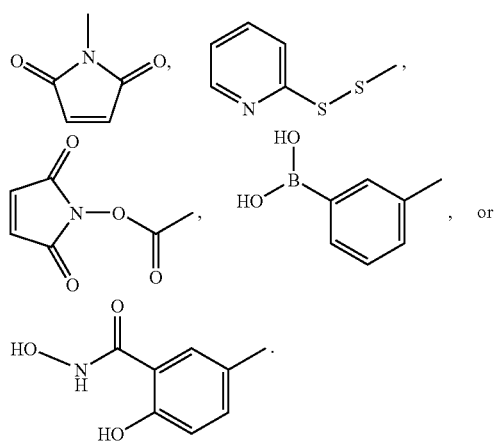

In one embodiment said amphiphilic block copolymer has a general formula selected from the group comprising

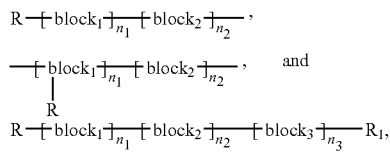

wherein block$_1$ and block$_3$ are hydrophilic,
block$_2$ is hydrophobic,
n$_1$, n$_2$, and n$_3$ are integer numbers from 2 to 20000, and
R and R$_1$ are functional groups as defined above.

In one embodiment said polymeric organic matrix component is a hydrophobic polymer.

In one embodiment said hydrophobic polymer is selected from the group, but not limited to, comprising polystyrenes (including substituted and modified styrenes), styrene copolymers, styrene-butadiene copolymers, polystyrene-based elastomers, polyethylenes, polypropylenes, polytetrafluoroethylenes, extended polytetrafluoroethylenes, polymethylmetacrylates, ethylene-co-vinyl acetates, polysiloxanes (e.g. polymethylsiloxanes, such as polydimethylsiloxane, polyphenylmethylsiloxanes, such as polyphenylmethylsiloxane, their copolymers and polymers based on them), polyethers, polyurethanes, polyether-urethanes, polyethylene terephthalates, polysulphones.

The objects of the present invention are also solved by a film comprising at least one of said polymeric nanoparticles as defined above, preferably a plurality of said polymeric nanoparticles, wherein said film is made of a polymer.

In one embodiment said polymer is a hydrophilic polymer selected from, but not limited to, polyethylene glycols, polyethylene oxides, polyacrylamides, polyacrylic acids and their related polymers and copolymers, acrylates, maleic anhydride copolymers, methacrylate, ethacrylate and related polymers, amine-functional polymers, such as polyethyleneimines, poly-2-ethyl-2-oxazolines and polyallylamines, ethers, such as polymethylvinyl ethers, polyepoxysuccinic acid, glycerol propoxylates, styrenes, such as polystyrenesulfonate and related polymers, vinyl acids, and vinyl alcohols, such as polyvinyl alcohols, poly(vinylpyrridine)s and poly(vinylpyrrolidone), as well as copolymers and combinations thereof.

In one embodiment said biological applications are selected from the group comprising labeling and/or detection of cells, biological (macro-)molecules or other analytes, fluorescence microscopy, (flow) cytometry, fluorescence-activated cell sorting (FACS), fluorescence resonance energy transfer (FRET), immunohistochemistry, clinical immunoassays, fluorescence-quenching-based enzyme-activity assays, high-throughput screening (e.g. using microarrays), molecular diagnostics (e.g. detection of amplified or non-amplified nucleic acids), and sensing of temperature, pressure, oxygen, and other substances that influence the up-conversion process in cells and tissues. Potential cellular targets include, but are not limited to bacteria and eukaryotic cells, in particular mammalian cells.

In one embodiment said biological (macro-)molecules or other analytes are selected from the group comprising nucleic acids/(poly-)nucleotides, such as DNA and RNA, (poly-)peptides/proteins, carbohydrates, lipids, glycoproteins, lipoproteins, viral and/or bacterial antigens, and pharmaceuticals.

The objects of the present invention are also solved by the use of a polymeric nanoparticle as defined above for biological applications as defined above.

The objects of the present invention are also solved by a polymeric nanoparticle as defined above for singlet oxygen generation.

The objects of the present invention are further solved by a polymeric nanoparticle as defined above for the treatment of diseases.

In one embodiment said disease is cancer.

In a preferred embodiment the polymeric nanoparticle as defined above is used for photodynamic therapy. Photodynamic therapy (PDT) is based on the accumulation of a photosensitizer in malignant tissues followed by illumination with light at an appropriate wavelength inducing photochemical reactions that result in tissue destruction. Usually, the photosensitizer is excited from a ground singlet state to an excited singlet state. It then undergoes intersystem crossing to a longer-lived excited triplet state. One of the few chemical species present in tissue with a ground triplet state is molecular oxygen. When the photosensitizer and an oxygen molecule are in proximity, an energy transfer can take place that allows the photosensitizer to relax to its ground singlet state, and create an excited singlet state oxygen molecule. Singlet oxygen is a very aggressive chemical species and will very rapidly react with any nearby biomolecules. (The specific targets depend heavily on the photosensitizer chosen.) Ultimately, these destructive reactions will kill cells through apoptosis or necrosis. As an example, PDT can be used for the treatment of basal cell carcinoma (BCC), which is the most common form of skin cancer in humans.

In one embodiment of the present invention, the above defined nanoparticle has a size in the range of 1-750 nm, preferably 5-500 nm, even more preferably 5-300 nm.

In one embodiment said at least one hydrophilic block of said amphiphilic block copolymer is selected from the group comprising polyethylene glycols, polyethylene oxides, polyacrylamides, polyacrylic acids and their related polymers and copolymers, acrylates, maleic anhydride copolymers, methacrylate, ethacrylate and related polymers, amine-functional polymers, such as polyethyleneimines, poly-2-ethyl-2-oxazolines and polyallylamines, ethers, such as polymethylvinyl ethers, polyepoxysuccinic acid, glycerol propoxylates, styrenes, such as polystyrenesulfonate and related polymers, vinyl acids, and vinyl alcohols, such as polyvinyl alcohols, as well as copolymers and combinations thereof.

In one embodiment said at least one hydrophobic block of said amphiphilic block copolymer is selected from the group comprising polystyrenes, styrene-butadiene copolymers, polystyrene-based elastomers, polyethylenes, polypropylenes, polytetrafluoroethylenes, extended polytetrafluoroethylenes, polymethylmetacrylates, ethylene-co-vinyl acetates, polymethylsiloxanes, such as polydimethylsiloxane, polyphenylmethylsiloxanes, such as polyphenylmethylsiloxane, polyethers, polyurethanes, polyether-urethanes, polyethylene terephthalates, polysulphones. In general, all biocompatible amides and imides, carbonates, dienes esters, ethers, olefins, vinyl acetals, vinyl esters, vinyl ethers and ketones, vinylpyridine and vinylpyrrolidone polymers, and ketones can be used.

Preferred amphiphilic block copolymers include, but are not limited to MePEG-b-PDLLA (methyl polyethylene glycol-block-poly-D,L-lactic acid), MePEG-b-PCL (methyl polyethylene glycol-block-polycaprolactone), MePEG-b-PLGA (methyl polyethylene glycol-block-polylactic-co-glycolic acid), PEO-PPO-PEO (polyethylene oxide-polypropylene oxide-polyethylene oxide), PEG-b-PBLA (polyethylene glycol-block-polybenzyl-L-aspartate), PS-b-PAA (polystyrene-block-polyacrylic acid), and PEO-b-PBD (polyethylene oxide-block-polybutadiene).

These copolymers can have varying hydrophilic and hydrophobic blocklengths.

The hydrophilic and hydrophobic block(s) of said amphiphilic block copolymer are bioinert, i.e. non-biodegradable, and non-toxic.

A particularly preferred amphiphilic block copolymer is PS-b-PAA (polystyrene-block-polyacrylic acid) with the general formula

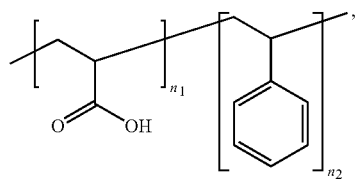

wherein $n_1$ and $n_2$ are integer numbers between 1 and 10000, preferably between 1000 and 8000.

In one embodiment said polymeric organic matrix component is a hydrophobic polymer. This hydrophobic polymer is miscible or highly compatible with the hydrophobic block(s) of the amphiphilic block copolymer. They can be, but do not have to be identical. As the hydrophobic block(s) of the amphiphilic block copolymer, it is bioinert, i.e. non-biodegradable, and non-toxic.

In an preferred embodiment said hydrophobic polymer is selected from the group comprising polystyrenes, styrene-butadiene copolymers, polystyrene-based elastomers, polyethylenes, polypropylenes, polytetrafluoroethylenes, extended polytetrafluoroethylenes, polymethylmetacrylates, ethylene-co-vinyl acetates, polymethylsiloxane, such as polydimethylsiloxane, polyphenylmethylsiloxanes, such as polyphenylmethylsiloxane, copolymers thereof as well as substituted and modified polysiloxanes, polyethers, polyurethanes, polyether-urethanes, polyethylene terephthalates, polysulphones.

A particularly preferred hydrophobic polymer is polystyrene (PS) having a molecular weight between $10^2$ and $10^9$. Preferred molecular weights are 400, 600, 800, 1000, 6000, 29000, and 100000, most preferably 400.

Preferably, said polymeric matrix is transparent in the range of from 300 to 1600 nm.

Preferably, said polymeric matrix is a solid, a gel or an oily fluid.

An "oily fluid" is a fluid with a viscosity equal or higher than $0.50 \times 10^{-3}$ Pa·s.

As used herein the term "gel" usually refers to a system wherein one (or several) component(s) (also termed as "network component(s)") is (are) dispersed as a colloid in another component, such as a solvent. Preferably, a "gel" is a colloidal system with a finite, usually rather small yield stress.

For example, in a polymer gel, the network component is a polymer, and the polymer may be colloidally dispersed in a solvent such as water to form a gel. The polymer network may be a network formed by covalent bonds or by physical aggregation with regions of local order acting as network junctions. The gel may be physical in which case the interactions between the molecules of the dispersed component(s) are non-covalent in nature, e.g. van der Waals interactions, or it may be chemical in which case the interactions between the molecules of the dispersed component(s) are covalent. Optionally the component may be physically or chemically crosslinked. In the case of physical crosslinking, there are no covalent bonds between the molecules but the dispersed component(s) is (are) physically intertwined. In the case of chemical crosslinking there are covalent bonds between the molecules of the dispersed component(s), which have been achieved by irradiation or the addition of chemical crosslinking agents.

Nanoparticles with a solid polymeric matrix can also be referred to as nanospheres. Nanoparticles with a gel or oily fluid polymeric matrix can also be referred to as nanocapsules.

In one embodiment said polymeric matrix is physically or chemically crosslinked (see above).

In one embodiment said polymeric matrix does not take part in a photon energy up-conversion process upon irradiation of said medium.

In one embodiment said first component is neither covalently bonded nor complexed to said second component.

In another embodiment said first component is covalently bonded or complexed to said second component.

In a preferred embodiment said first and said second organic compounds are different compounds.

Preferably, said emissive component's emitting light at said second wavelength region $\lambda_2$ is due to an up-conversion process based on direct or sequential two-photon excitation or on direct or sequential multi-photon excitation or on excitation of molecules populating high vibrational state(s) ("hot-band absorption"), which up-conversion process occurs upon absorption of light by said first component at said first wavelength region $\lambda_1$, or said emissive component's emitting light at said second wavelength region $\lambda_2$ is due to an up-conversion process based on a triplet-triplet annihilation process between photoexcited molecules of said emissive component and/or based on a triplet-triplet annihilation process between photo-excited molecules of said first component.

In a preferred embodiment said second wavelength region $\lambda_2$ is in the range 360-750 nm and said first wavelength region $\lambda_1$ is in the range 450-1600 nm.

In one embodiment of the present invention said first component is an organic dye or molecule having a populated triplet or mixed triplet-singlet state, a two-photon-absorbing (TPA)-dye, an optical limiting compound, another molecule with a populated triplet state or an optical limiting compound—e.g. a fullerene, or carbon nanotubes.

In one embodiment said second component is an organic dye.

Preferably, said first component is a first organic dye and said second component is a second organic dye, wherein said first and second organic dyes are the same or different.

In one embodiment said first and/or said second organic dye is selected from the group comprising organic dyes with populated triplet states or capable of direct and/or sequential two-photon excitation, organic dyes capable of direct and/or multi-photon excitation, organic dyes capable of non-linear absorption and organic dyes capable of hot-band absorption.

In one embodiment said organic dye, in particular said first organic dye, is selected from the group comprising organic molecules having populated triplet states and especially metal-organic complexes having populated triplet states, for example but not limited to Li, Mg, Al, Ti, V (VO), Mn, Fe, Co, Ni, Cu, Zn, Ga, Ru, Pd, Ag, Re, Os, Ir, Pt, Pb, U (UO$_2$) containing organic complexes, or any combination of the foregoing to ensure wavelength control.

Preferably, said first organic dye is selected from the group comprising compounds with a populated triplet state, including but not limited to
porphyrins, including extended porphyrins, texaphyrins, sapphyrins, orangerins (any carbon-bridged pyrrolic system), substituted porphyrins and any of the foregoing molecules (porphyrins) containing metals including but not limited to Li, Mg, Al, Ti, V (VO), Mn, Fe, Co, Ni, Cu, Zn, Ga, Ru, Pd, Ag, Re, Os, Ir, Pt, Pb, U (UO$_2$)
phtalocyanines, including extended phtalocyanines, substituted phtalocyanines, and any of the foregoing phtalocyanines containing metals including but not limited to Li, Mg, Al, Ti, V (VO), Mn, Fe, Co, Ni, Cu, Zn, Ga, Ru, Pd, Ag, Re, Os, Ir, Pt, Pb, U (UO$_2$)
benzopyridines, benzopyrizines, quinolates and hydroxyquinolates, acetyl-acetonates, substituted benzopyridines, benzopyrizines, quinolates and hydroxyquinolates, acetyl-acetonates; —mixtures of any of the foregoing,
and said second organic dye is selected from the group comprising compounds showing fluorescence emission in the range of from 360 to 750 nm, in particular fluorescent dyes showing fluorescence emission in the range of from 360 nm to 750 nm, e.g.
anthracenes, tetracenes, pentacenes, perylenes
substituted anthracenes, tetracenes, pentacenes, perylenes
phenyl (bi-, tri-phenyl)-bridged anthracenes, tetracenes, pentacenes, perylenes
fluorenes, thiophenes,
polyfluorenes and oligofluorenes, with or without any sidechain pattern and their copolymers, polyparaphenylenes, including polyparaphenylene vinylene, and polyphenyleneethinylenes.

Particularly preferred sensitizers are

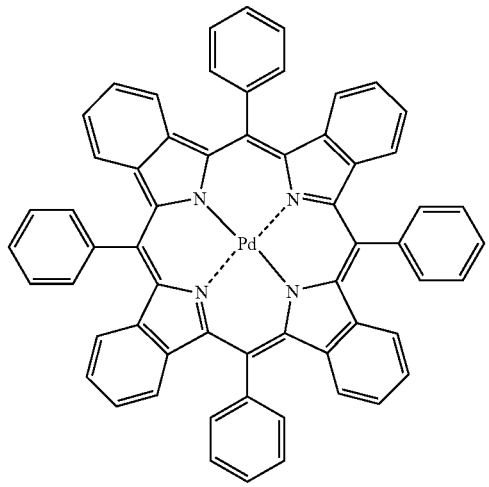

$C_{60}H_{36}N_4Pd$
Exact Mass: 918,20
Mol. Wt.: 919,37
C, 78, 38; H, 3, 95; N, 6, 09; Pd, 11,58
PdTBP (meso-tetraphenyl-tetrabenzoporphyrin palladium) and

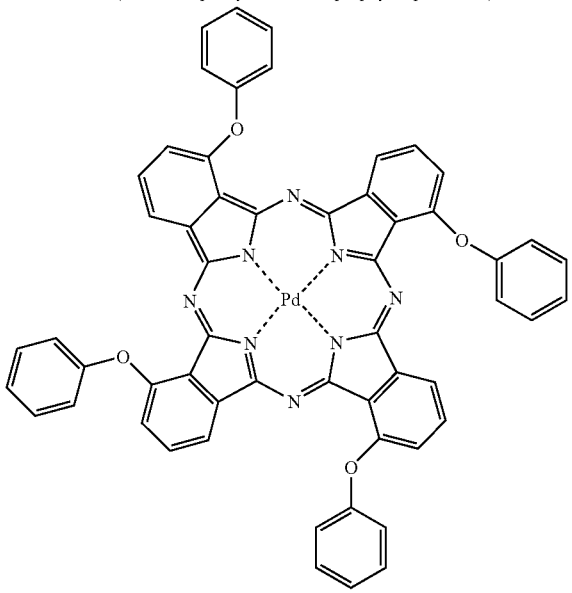

Exact Mass: 986,16 gmol$^{-1}$
PdOPhPc (palladium(II) 1,8,15,22-tetraphenoxy-phthalocyanine).

Particularly preferred emitters are

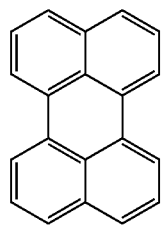

$C_{20}H_{12}$
Exact Mass: 252.09
Mol. Wt.: 252.31
C, 95.21; H, 4.79
Perylene (dibenz[de,kl]anthracene), -continued

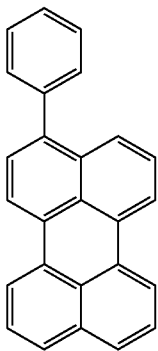

C₂₆H₁₆
Exact Mass: 328,13
Mol. Wt.: 328,41
C, 95.09; H, 4.91
PhP, (3-phenyl-perylene),

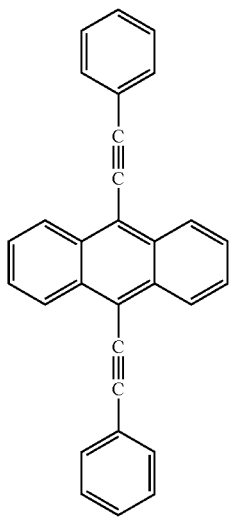

C₃₀H₁₈
Exact Mass: 378.14
Mol. Wt.; 378.46
C, 95.21: H, 4.79
BPEA (9,10-bis(phenylethynyl)anthracene) and

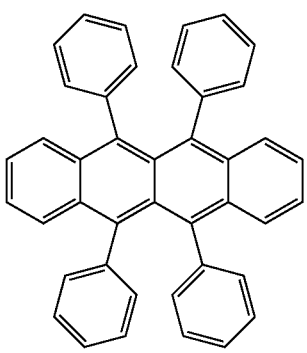

C₄₂H₂₈
Exact Mass: 532.22
Mol. Wt.; 532.67
C, 94.70; H, 5.30
Rubrene (5,6,11,12-tetraphenylnaphthacene).

In one embodiment said first and said second organic dye are chosen such that a populated triplet state of said sensitizer is at an energy level allowing a triplet-triplet transfer to the triplet levels of the emitter. The subsequent triplet-triplet annihilation between triplets of the emitter allows to populate the singlet state of the emitter and to emit upconverted photons.

Preferably, combinations of said first and second component (sensitizer and emitter, respectively) are selected from the following:

1. Perylene/PdTBP—blue emission
2. PhP/PdTBP—blue emission but red-shifted in comparison to 1.
3. BPEA/PdTBP—green emission
4. Rubrene/PdOPhPc—yellow emission
5. Rubrene/PdTBP—yellow emission Additional embodiments of preferred sensitizer components and emissive components and are described in the following:

Sensitizer Molecules (or "Sensitizer Components")

A "sensitizer" is a molecule which is able to absorb light, the sensitizer being either an organic dye or a metal-organic complex, preferably with a high populated triplet states.

A metal-organic complex is per definition a compound containing at least a metal M surrounded by one or more molecules, the so-called ligands L which are generally bound to the metal ion by a coordinate covalent bond.

The ligands are organic molecules, cyclic or acyclic, aromatic or non-aromatic, monodentate or polydentate.

In case they are extended aromatic systems they are themselves organic dye sensitizers without being bound to a metal.

For better understanding:

Both, the Pd-porphyrine (=metal organic complex) but also the metal-free porphyrine (=Organic molecule) are sensitizers.

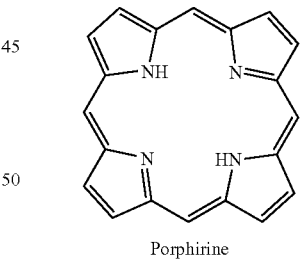

Porphirine

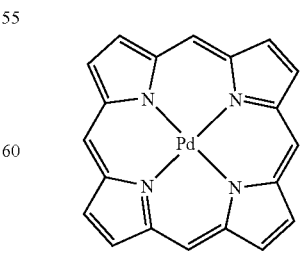

Pd-Porphirine

The metal-organic complexes can be
mononuclear with the general structure $ML_m$
with m being the number of ligands m=1-8, preferably 1-3
or
polynuclear complexes with metals bridge via a common ligand B with general structure $L_mM\text{-}[B\text{-}ML_m]_n$, with Lm, at each occurrence in this formula, being an independently selected ligand.
n being the repeating unit 1-10, preferably 1-3
and with B being any bridging organic molecule acting as polydentate ligand or a halogenide such as F, Cl, Br, I
polynuclear complexes with ligands bridged via A
with general structure $ML_m\text{-}[A\text{-}L_mM]_n$, with Lm, at each occurrence in this formula, being an independently selected ligand.
n being the repeating unit 1-6, preferably 1-3
and with A being defined as

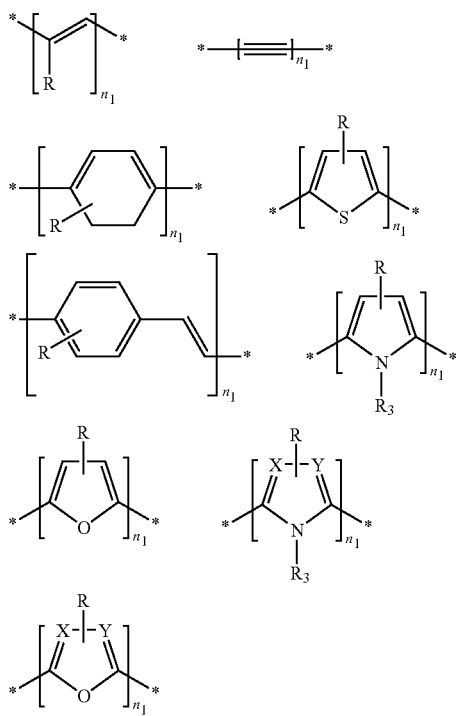

or any combination of these units, or any other organic unit forming fused system while bridging the ligands
R being H, any substituted or non-substituted alkyl, aryl or heteroaryl
$n_1$ being 0-10, preferably 0-2
$R_3$ being H, $-(CH_2)_nCH_3$, $-(CH_2)_n-COOR$, $-(CH_2)_n-OR$, $-(CH_2)_n-SR$, $-(CH_2)_n-NR_2$, $-((CH_2)_p-O)_n-CH_3$, The metal M is selected for example, from Li, Na, K, Mg, Ca, Sr, Al, Ga, In, Ti, Sn, Pb, Zr, Hf, V, Nb, Cr, Mo, W, Mn, Re, Fe, Ru, Os, Co, Rh, Ir, Ni, Pd, Pt, Cu, Ag, Au, Zn, Cd, Hg, Yb, Eu, Nd, Gd, Th
preferably Pd, Pt, Ru, Os, Re, The ligand L can be selected for example, but not limited thereto, from the group of
heterocyclic aromatic or non-aromatic systems containing at least one atom which is not carbon, preferably nitrogen or oxygen, by which the ligand is linked to the metal. The said aromatic heterocyclic aromatic or non-aromatic system is a mono- or polycyclic condensed ring system or a system of rings covalently bonded to each other, wherein, optionally, said ring system or rings are substituted with further substituents Z, with Z being one or more moieties which, at each occurrence, is independently selected from H, substituted or non-substituted aryl group, alkyl, alkenyl or alkynyl, or halogen, such as Cl, Br, F, I, or $NO_2$, $NH_2$, CN, $SO_3H$, OH, H, $-(CH_2)_nCH_3$, $-(CH_2)_n-COOR$, $-(CH_2)_n-OR$, $-(CH_2)_n-SR$, $-(CH_2)_n-NR_2$, $-((CH_2)_p-O)_n-CH_3$, with R being H, any substituted or non-substituted alkyl, aryl or heteroaryl n being 0-10, preferably 0-6 and p being 0-4, preferably 1-2 or any aromatic and heteroaromatic system, preferably represented by

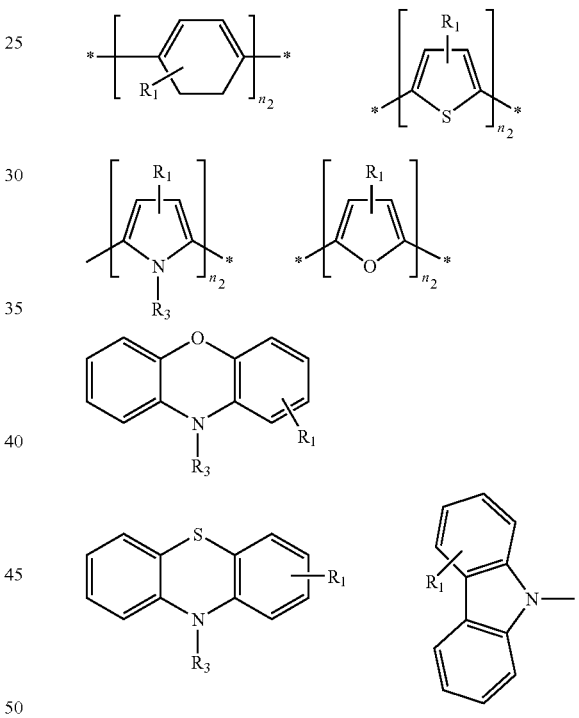

$n_2$ being 1-5

$R_1$ being H, any alkenyl, alkynyl, aryl or halogen, such as Cl, Br, F, I, or $NO_2$, $NH_2$, $-CN$, $-SCN$, $=C(CN)_2$, $=O$, $-SO_3H$, OH, H, $-(CH_2)_nCH_3$, $-(CH_2)_n-COOR$, $-(CH_2)_n-OR$, $-(CH_2)_n-SR$, $-(CH_2)_n-NR_2$, $-((CH_2)_p-O)_n-CH_3$, $R_3$ being H, $-(CH_2)_nCH_3$, $-(CH_2)-COOR$, $-(CH_2)_n-OR$, $-(CH_2)_n-SR$, $-(CH_2)_n-NR_2$, $-((CH_2)_p-O)_n-CH_3$, The ligand L can be selected for example, but not limited thereto, from the class of substituted or non-substituted macrocyclic systems of porphyrines including and also extended systems of these derivatives, such as benzoporphyrines or naphthaloporphyrine.

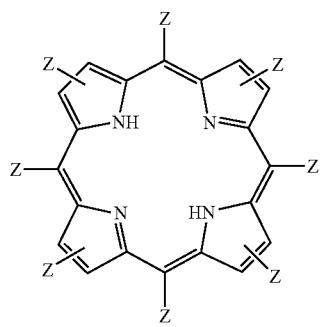

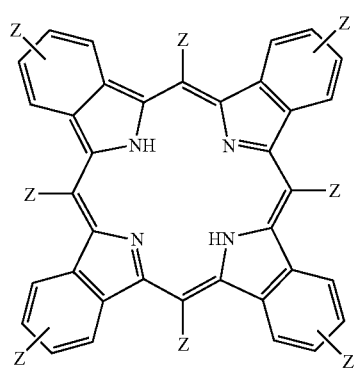

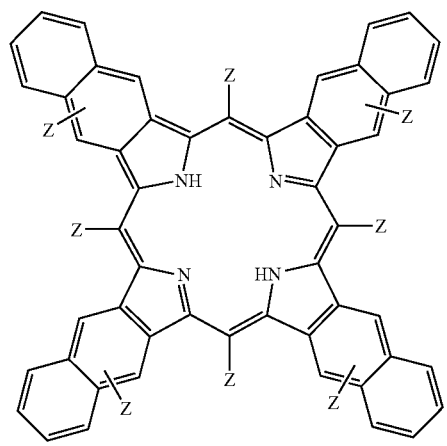

The ligand L can be selected for example, but not limited thereto, from the class substituted or non-substituted macrocyclic systems of tetraazaporphyrine, phthalocyanine or naphthalocyanine.

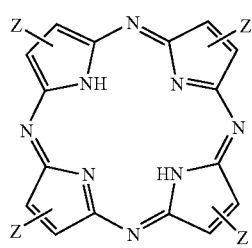

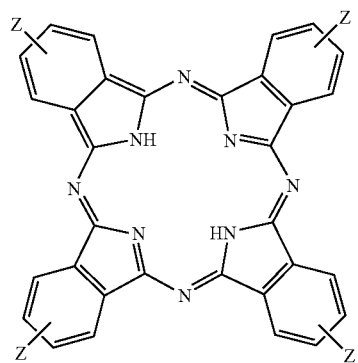

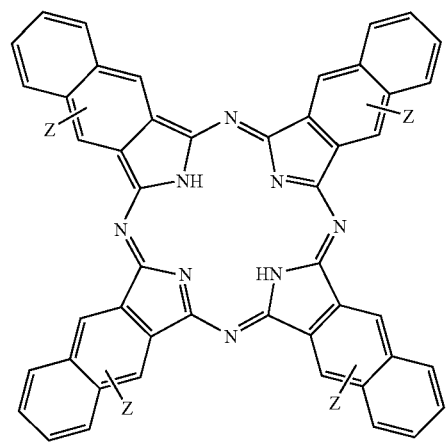

The ligand L can be selected for example, but not limited thereto, from the class of substituted or non-substituted macrocyclic systems of corroles or aza-corroles including their benzo- and naphto-extended systems.

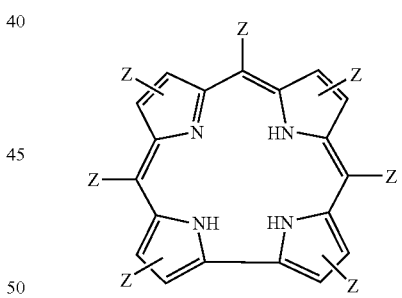

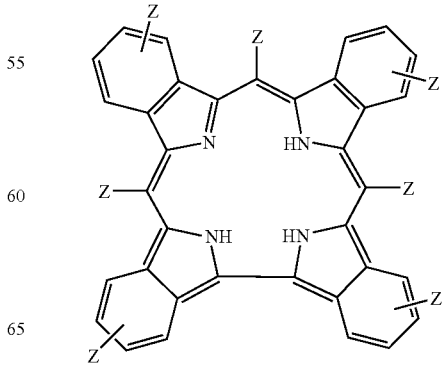

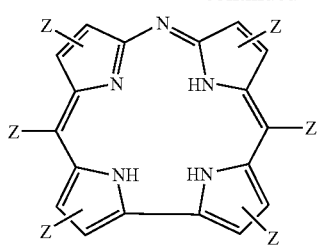
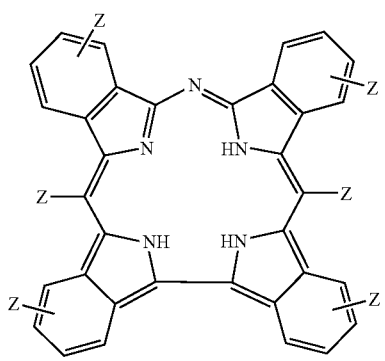
The ligand L can be selected for example, but not limited thereto, from the class of substituted or non-substituted linear tetra-, tri- or dipyrrole systems, including their benzo- and naphto-extended systems
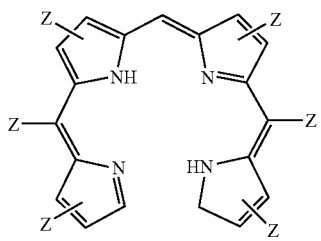
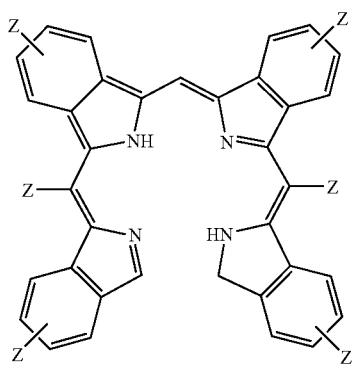
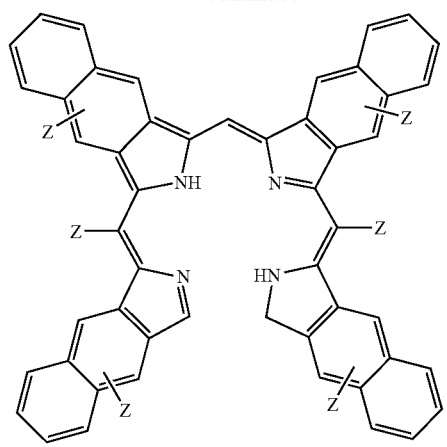
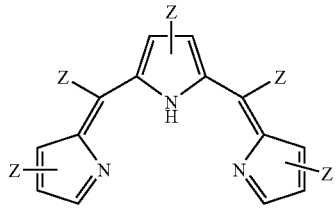
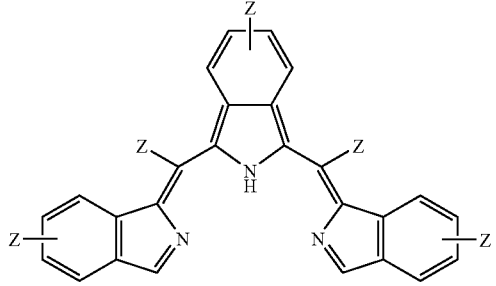
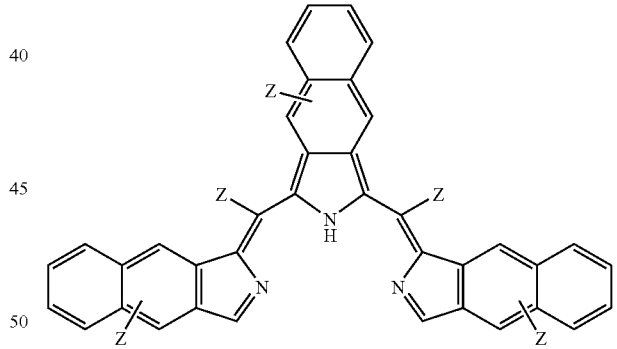
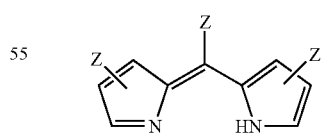
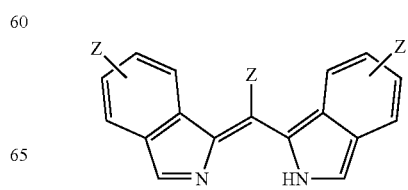

-continued

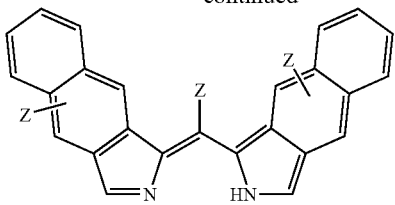

The ligand L can be selected for example, but not limited thereto, from the class of substituted or non-substituted pyridine, bi-, ter- or poly-pyridyls, phenantrolines, quinoline, isoquinoline, bis-isoquinoline, hydroxyquinoline

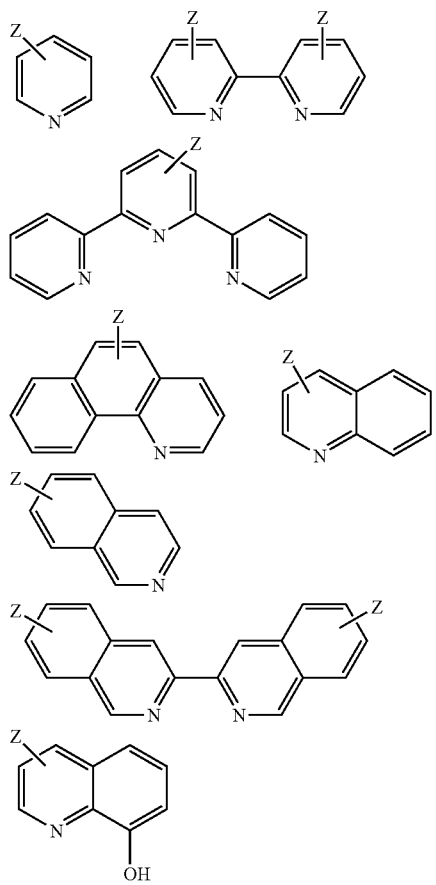

The ligand L can be selected for example, but not limited thereto, from class of substituted or non-substituted heteroaromatics molecules represented by the structures and any combination of the structures

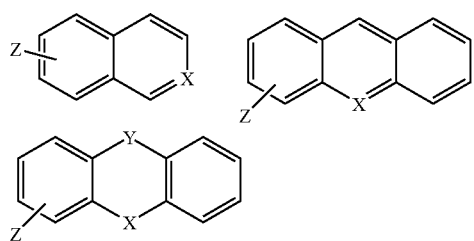

-continued

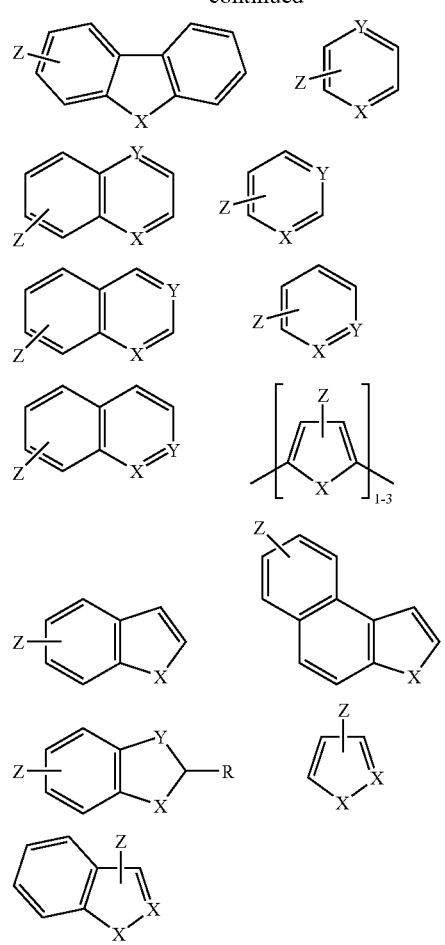

with X and Y being independent from each other NR, O, S

The ligand L can be selected for example, but not limited thereto, from derivatives containing substituted or non-substituted benzene-1,2-diol; benzene-1,2-diamine; ethane-1,2-diamine; ethane-1,2-diol; naphthalene-2,3-diamine; naphthalene-2,3-diol; anthracene-2,3-diol; anthracene-2,3-diamine; oxalamide, oxalic acid, ethylendiamintetraacetic acid

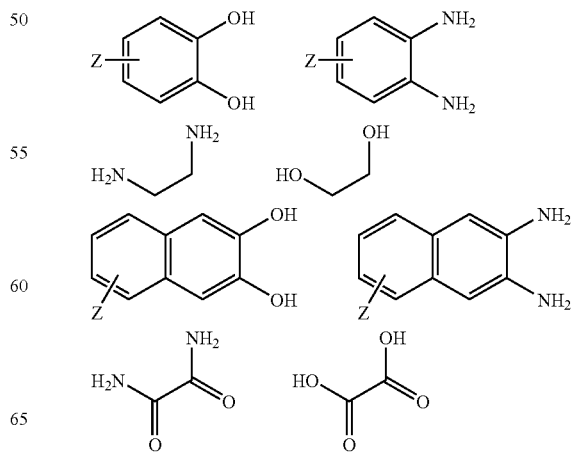

-continued

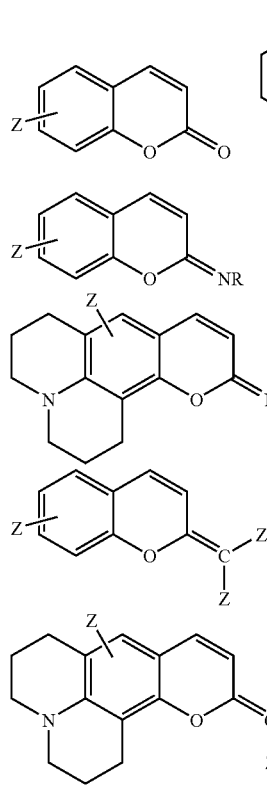

Sensitizers which are organic dyes are selected, but not limited thereto, from the class of substituted or non-substituted coumarins and their derivatives, substituted or non-substituted cyanine-, merocyanine-, and azo-dyes and their derivatives,

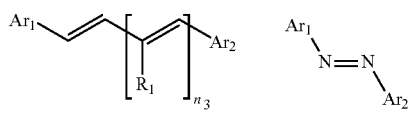

with $n_3$=0-6, preferably 0-3

With $Ar_1$ and $Ar_2$ being same or different, at each occurrence independently selected from

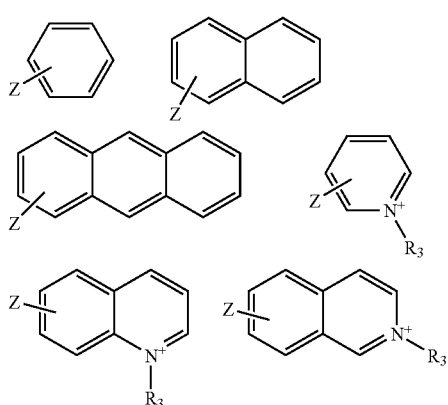

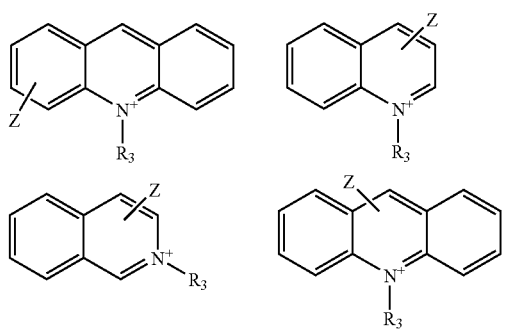

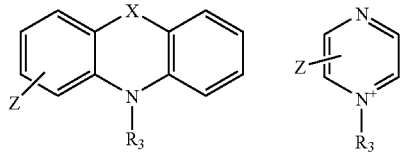

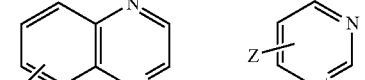

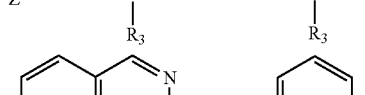

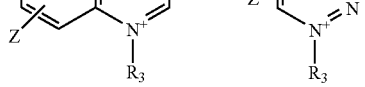

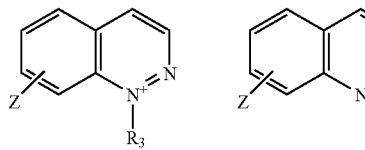

with Z as described above

-continued

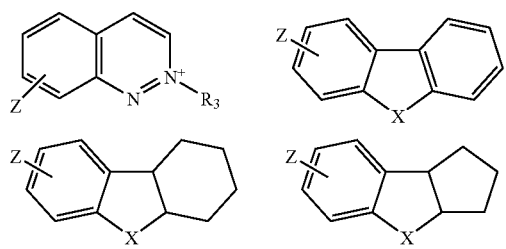
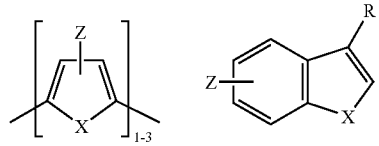
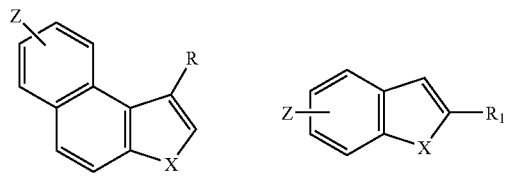
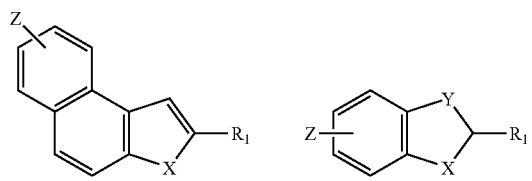
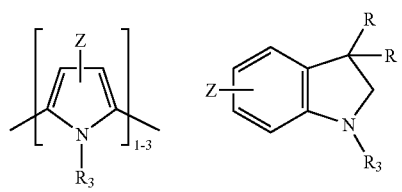
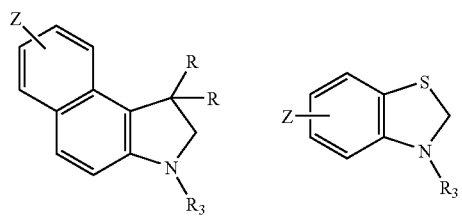
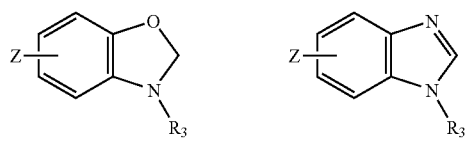
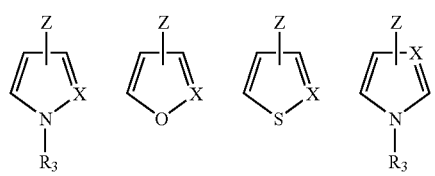
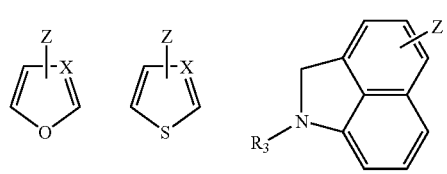

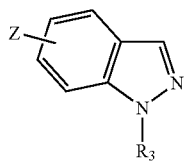
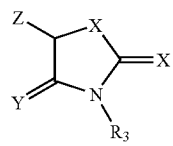

or any combination of these structures
with Z, R, and $R_3$ as defined above
substituted or non-substituted derivatives of squarylium and croconium dyes

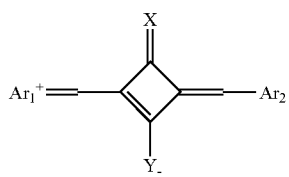

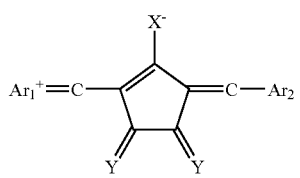

X, Y, $Ar_1$ and $Ar_2$ being defined as above,
substituted or non-substituted derivatives of semi-squarylium or semi-croconium dyes and their derivatives
or

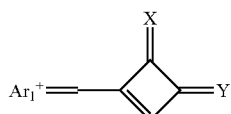

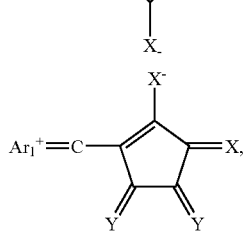

or any aromatic and heteroaromatic systems bridged (poly-)styrene, or other aromatic or heteroaromatic rings, secondary or tertiary amines with aromatic or heteroaromatic systems attached, (poly-)phenylenes mono-endcapped with an aromatic system or metal organic complexes, or substituted and non-substituted derivatives of a) a (poly-)phenylenes mono-endcapped with an aromatic system, or b) a secondary or tertiary amines substituted with aromatic or heteroaromatic unit, or c)-f) aromatic and heteroaromatic systems bridged by (poly-)styrene, or other (poly-)aromatic or heteroaromatic rings, as presented by structures below a)

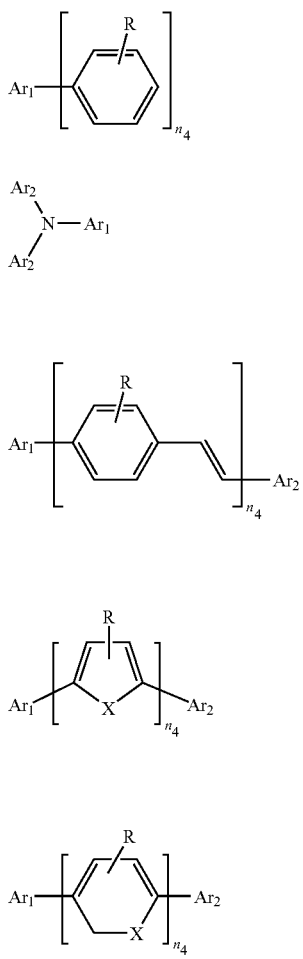

b)

c)

d)

e)

with $n_4=1-4$, preferably 1-2

$Ar_1$, $Ar_2$, X and R as described above.

Organic dye can be also selected from the class of ligands L, such as the class of porphyrine, phtalocyanine, corroles, which are not bound to a metal.

Emitter Molecules (or "Emissive Components")

are organic molecules with emitting singlet states (efficient)

The emitter molecules can be selected from the group of E.

E can be selected for example but not limited from the class of substituted or non-substituted anthracenes, naphtacenes, pentacenes, rubrene and their derivatives, the core being expressed by the structures

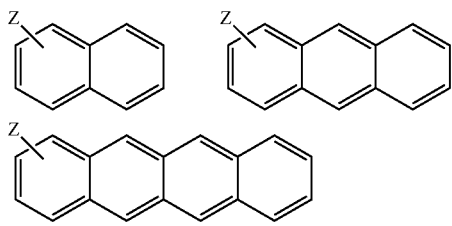

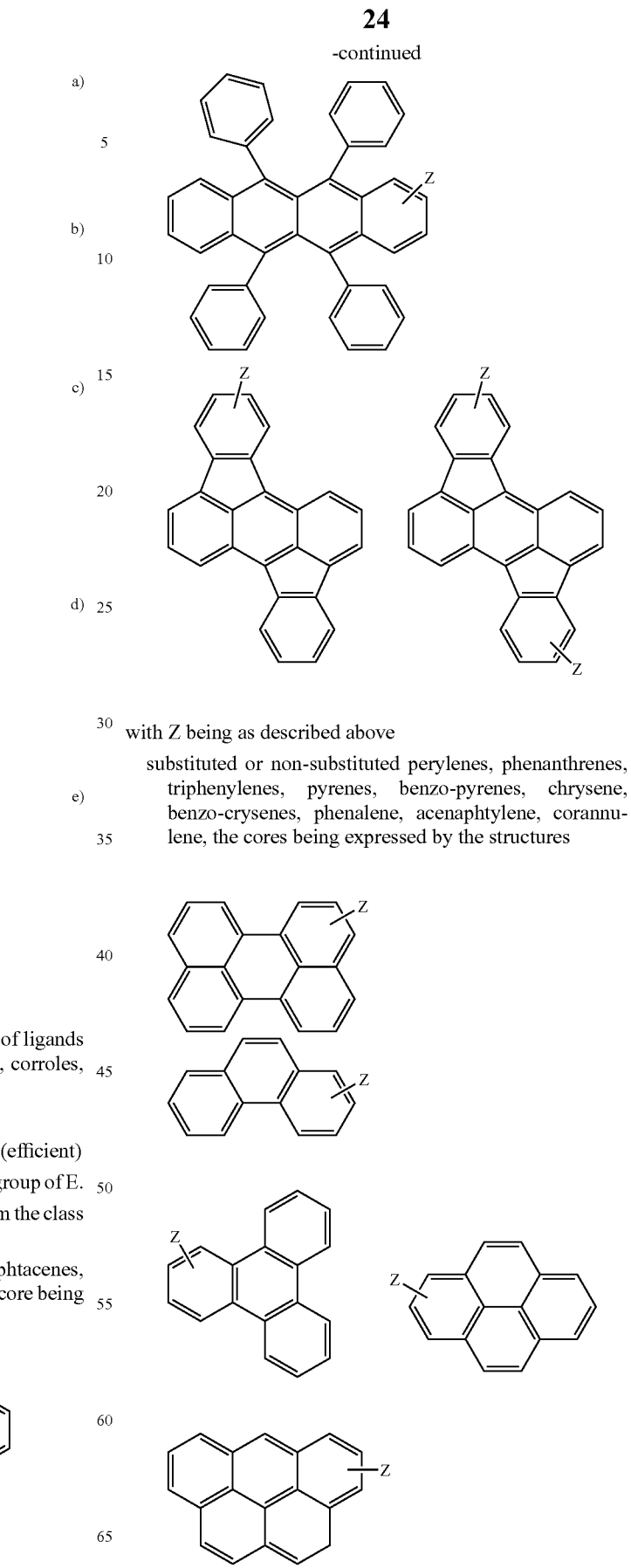

with Z being as described above substituted or non-substituted perylenes, phenanthrenes, triphenylenes, pyrenes, benzo-pyrenes, chrysene, benzo-crysenes, phenalene, acenaphtylene, corannulene, the cores being expressed by the structures -continued

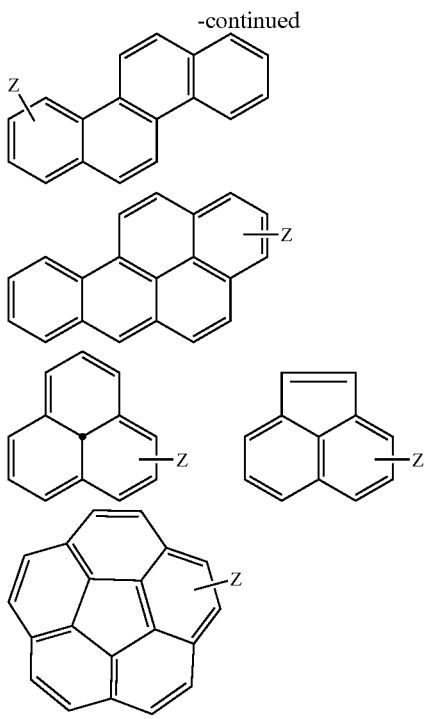

with Z being as described above
substituted or non-substituted of derivatives containing non-aromatic, aromatic and heteroaromatic fused systems,
the cores being expressed by the structures

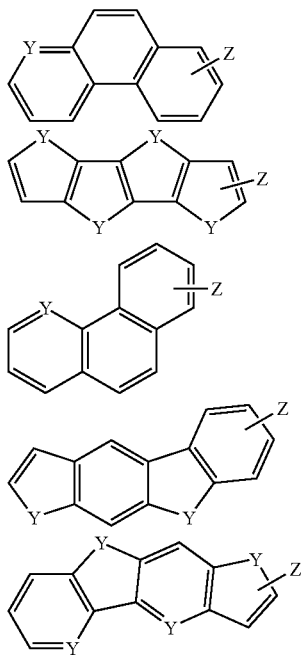

or any combination of these structures
with Z being as described above
with Y being C, Si, N, S, O
substituted or non-substituted of class of (poly)-silole or -pyrrol or thiophene based compounds, the cores being expressed by the structures

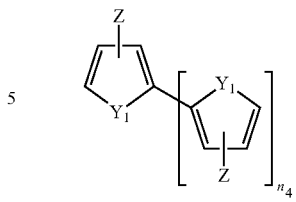

with Z and $n_4$ as described above
and Y1 being $Si(Z)_2$, —N(Z) or S.

The emitter molecules can be also molecules expressed by the general formula

E-A-[E-A]$_p$-E with p being 0 to 20
with E and A as defined above and with Lm, when appearing, at each occurrence in this formula, being an independently selected ligand.

In a preferred embodiment of the present invention said first and said second components are homogeneously distributed within said matrix.

The objects of the present invention are also solved by a method of producing the polymeric nanoparticle as defined above, said polymeric nanoparticle comprising a medium for photon up-conversion and a stabilizing agent, said medium comprising at least two components and a polymeric organic matrix component, said polymeric organic matrix component forming a polymeric matrix in which polymeric matrix said at least two components are distributed, wherein a first component of said at least two components is capable of absorbing light at a first wavelength region $b \leq \lambda_1 \leq x$, which first component acts as a sensitizer in said medium, and wherein a second component of said at least two components is capable of emitting light at a second wavelength region $y \leq \lambda_2 \leq z$, which second component acts as an emissive component in said medium, wherein $\lambda_2 \leq \lambda_1$, and wherein, upon absorption of light by said first component at said first wavelength region $b \leq \lambda_1 \leq x$, said emissive component emits light at said second wavelength region $y \leq \lambda_2 \leq z$, wherein said first component and said second component are organic compounds, said stabilizing agent being as defined above, said method comprising the steps:

a) providing, in any order, said first component, said second component, said polymeric organic matrix component, and said stabilizing agent, and mixing said first component, said second component, said polymeric organic matrix component and said stabilizing agent to give a mixture, b) inducing said mixture to form polymeric nanoparticles, thereby incorporating said medium for photon up-conversion into said nanoparticles.

In one embodiment step b) occurs by a process selected from emulsification, preferably emulsification followed by solvent evaporation or emulsification followed by solvent diffusion, salting out and solvent displacement.

In one embodiment of the method, said stabilizing agent is an amphiphilic block copolymer, preferably comprising at least one hydrophobic block and at least one hydrophilic block.

In one embodiment of the method, in step a), said first component, said second component, said polymeric organic matrix component and said amphiphilic block copolymer are dissolved in an organic water-miscible solvent forming a solution of said first component, said second component, said polymeric organic matrix component and said amphiphilic block copolymer.

In one embodiment of the method, after dissolving said first component, said second component, said polymeric organic matrix component and said amphiphilic block copolymer in said organic water-miscible solvent, said solution is rapidly mixed in step b) with an aqueous phase over a time period of $\leq 5$ s, preferably $\leq 2$ s, more preferably $\leq 1$ s, thereby inducing formation of said nanoparticles.

In one embodiment of the method, the amount of said aqueous phase with which said solution is rapidly mixed is in excess of the amount of said solution.

In one embodiment of the method, the amount of said aqueous phase is $\geq 2$ times, preferably $\geq 3$ times, more preferably $\geq 4$ times the amount of said solution.

In one embodiment of the method, said rapid mixing in step b) is achieved using pressure under which said aqueous phase and said solution are mixed, preferably using a jet mixer or a microfluidic device or two storage reservoirs which can be operated under pressure to eject a flow of liquid into a mixing reservoir, each of said storage reservoirs containing one of said aqueous phase and said solution and being operated to eject said aqueous phase and said solution into said mixing reservoir.

In one embodiment of the method, the concentration of said first component in said mixture, preferably the concentration of said first component is in the range of from 1 µM to 1 mM as calculated concentration in the photon upconversion medium.

In one embodiment, the concentration of said second component in said mixture, preferably the concentration of said second component is in the range of from 1 µM to 100 mM as calculated concentration in the photon upconversion medium.

In one embodiment, the concentration of said polymeric organic matrix component, in said mixture, preferably the concentration of said polymeric organic matrix component in said organic water-miscible solvent, is in the range of from 0 mg to 1000 mg per ml solvent.

In one embodiment, the concentration of said stabilizing agent in said mixture, preferably the concentration of said stabilizing agent in said organic water-miscible solvent is in the range of from 0.01 mg to 100 mg per ml solvent.

The term "the concentration of x is in the range of from 1 µM to 1 mM as calculated concentration in the photon upconversion medium" is meant to refer to the molar concentration of x in the finished, i.e. ready nanoparticle.

It should be noted that in some embodiments, the polymeric organic matrix component is not present in the sense that it is not, as such, added to the mixture upon production of the nanoparticle. In this case, the polymeric matrix in the nanoparticle is formed by the hydrophobic part of the stabilizing agent, preferably by the hydrophobic block of the amphiphilic block copolymer.

In one embodiment of the method, said organic water-miscible solvent is selected from acetone, tetrahydrofurane, and benzyl alcohol.

In one embodiment the method according to the present invention comprises the additional step(s)
  c) removing solvent present after step b), preferably to dryness, and/or, optionally,
  d) adding an aqueous phase, preferably water, to said nanoparticles.

In one embodiment of the method, step b) occurs by emulsion polymerization and in step a), said polymeric organic matrix component is provided in the form of monomers, which, in step b) are induced to polymerize and thereby form polymeric nanoparticles.

The objects of the present invention are also solved by a polymeric nanoparticle comprising a medium for temperature sensing and a stabilizing agent, said medium comprising a sensitizer component and a polymeric organic matrix component, said polymeric organic matrix component forming a polymeric matrix in which polymeric matrix said sensitizer component is distributed, wherein said medium for temperature sensing does not comprise an emissive component, wherein said sensitizer component and said emissive component are as defined above, said stabilizing agent also being as defined further above. Such polymeric nanoparticle for temperature sensing is herein also sometimes referred to as a temperature sensing (TS) nanoparticle. In contrast thereto a polymeric nanoparticle for photon-up-conversion, as defined further above, is herein also sometimes referred to as up-conversion (UC) nanoparticle. Such UC nanoparticle comprises a medium for photon up-conversion including a sensitizer and an emissive component and a polymeric organic matrix component, and a stabilizing agent, all as defined further above.

As used herein, the terms "sensitizer component" and "sensitizer" are used interchangeably. The same applies to the terms "emissive component" and "emitter", which are also used interchangeably with each other. The objects of the present invention are also solved by a method of producing a temperature sensing nanoparticle, as defined above, which method is identical to the method of producing a polymeric nanoparticle for photon up-conversion, except for that no emissive component is included in the production of such temperature sensing nanoparticle.

The term "hydrophilic polymer", as used herein is meant to refer to a polymer that contains hydrophilic units or groups or blocks, e.g. ethyleneoxide, carboxyl, hydroxyl, amino. Such hydrophilic polymers can therefore easily dissolve in water or aqueous solutions.

The term "amphiphilic polymer", as used herein, is meant to refer to a polymer having distinct polar (hydrophilic) and nonpolar (hydrophobic) regions or blocks. Such distinct polar and non-polar regions in the molecule promote the formation of micelles in dilute aqueous solutions. For example, an amphiphilic polymer may contain a large organic cation or anion, such as $H_3C(CH_2)nCO_2^-$ or $H_3C(CH_2)nSO_3^-$ or $H_3C(CH_2)_nN(CH_3)_3^+$, which possesses a long unbranched hydrocarbon chain, n>7.

Incorporating certain amounts of hydrophobic comonomers into a hydrophilic polymer leads to an amphiphilic (or synonymously: amphipatic) copolymer that prefers to be located at interfaces between oil and water.

As used herein the term "organic" is used in its generally understood meaning, i.e. it refers to compounds which are carbon-containing compounds. As it is used here, it also includes elemental carbon, at least in the form of fullerenes. The term "organic" is further meant to exclude specific carbon-containing compounds such as: hydrogen-free chalkogenides of carbon, e.g. CO, $CO_2$, $CS_2$, and derivatives thereof, e.g. $H_2CO_3$, KSCN; further excluded are salt-like carbides which are binary compounds of elements with carbon, which decompose to hydrocarbons under the influence of water or dilute acids. Salt-like carbides have the general formula $M^I_2C_2$ or $M^{II}C_2$, wherein $M^I$ or $M^{II}$ denotes a metal ion with one or two valences. Salt-like carbides of calcium, silver and copper decompose to acetylene, the salt-like carbide of aluminum ($Al_4C_3$) decomposes to methane. Further excluded carbon-containing compound which do not form part of the term "organic" are metallic carbides, which are non-stoichiometric compounds having the character of an alloy. They are resistant to acids and are electrically conducting.

The inventors have found that it is possible to include a stabilizing agent into a polymeric nanoparticle said nanoparticle comprising a photon up-conversion medium (or a temperature sensing medium), wherein the stabilizing agent acts as a surfactant and prevents the nanoparticles from forming aggregates. The stabilizing agent ensures steric stabilization. If the nanoparticles are prepared via emulsification, the stabilizing agent also acts as an emulsifier. In preferred embodiments, the stabilizing agent is a hydrophilic polymer or a polymer having a hydrophobic part and a hydrophilic part, wherein the hydrophobic part also forms part of the organic polymeric matrix of the nanoparticle or, in fact, is the organic polymeric matrix of said nanoparticle. In other words, the polymeric matrix of said nanoparticle is formed by either a polymeric organic matrix component, or by the hydrophobic part of said stabilizing agent or by both. The polymeric organic matrix component is separate from the hydrophobic part of the stabilizing agent, but, chemically, the two may be identical. In order for a polymeric nanoparticle to form in accordance with the present invention, it suffices if only one of the two, i.e. either the polymeric organic matrix component or the hydrophobic part of the stabilizing agent, is present. It should be noted that the polymeric organic matrix component and the hydrophobic part of the stabilizing agent may be chemically identical, i.e. they may be the same chemical compound, or they may be different chemical compounds. In preferred embodiments, the stabilizing agent is a polymer selected from hydrophilic polymers, amphiphilic co-polymers, hydrophobic polymers with a covalently attached hydrophilic part, hydrophilic polymers with a covalently attached hydrophobic part, and polyelectrolytes having a hydrophobic part. Preferably, said polymer is an amphiphilic copolymer selected from amphiphilic block, graft, random and alternating copolymers, preferably an amphiphilic block copolymer or an amphiphilic graft copolymer. The hydrophobic part of the stabilizing agent is a hydrophobic block in case that the stabilizing agent is an amphiphilic block co-polymer or an amphiphilic graft co-polymer.

In a polymeric nanoparticle in accordance with the present invention, there is a core formed by the polymeric matrix and a shell surrounding said core. In preferred embodiments, the polymeric nanoparticle according to the present invention is made using an amphiphilic block co-polymer as stabilizing agent. The amphiphilic block co-polymer comprises at least one hydrophobic block and at least one hydrophilic block. Preferably, the hydrophobic block forms part or all of the polymeric organic matrix and hence of the aforementioned core of the nanoparticle. The hydrophilic block of the amphiphilic block co-polymer forms the aforementioned hydrophilic shell surrounding the core of said polymeric nanoparticle. In addition to the hydrophobic block of the amphiphilic block co-polymer present in said polymeric matrix or forming said polymeric matrix, there may also be additionally a polymeric organic matrix component present which also contributes to the formation of said polymeric matrix. The polymeric organic matrix component and the hydrophobic block of the amphiphilic block co-polymer may be chemically the same compound or they may be different compounds, provided, however, that they contribute to the formation of the polymeric matrix.

As outlined above, the aforementioned shell is preferably made of the hydrophilic block of an amphiphilic block co-polymer, and said functional group(s) is (are) covalently linked to said hydrophilic block, thus allowing for surface modification and biocompatibility of the nanoparticles.

The present inventors have devised a way in which a photon energy up-conversion system, sometimes here in also abbreviated as "photon up-conversion" system is incorporated into a polymeric nanoparticle. This makes the photon up-conversion system amenable to further handling in a number of environments depending on the individual structure of these nanoparticles. To the best knowledge of the present inventors, this is the first time that organic polymeric nanoparticles comprising a photon up-conversion medium have been devised.

The term "polymeric" as used herein in the context of a nanoparticle, is meant to refer to a nanoparticle which comprises a polymer or is made up of such polymer. The polymer in this case may be a polymeric organic matrix component, or it may be the stabilizing agent, or it may be both. The term "polymeric" is also meant to include the term "oligomeric". Both terms are used interchangeably herein and are meant to refer to a substance composed of molecules characterized by the multiple repetition of one or more species of monomers. A "multiple repetition of monomers", as used herein, is meant to refer to at least two, preferably 10 or more, more preferably 100 or more monomers linked to each other.

It should be noted that in embodiments of the nanoparticles according to the present invention, the first component and the second component, i.e. sensitizer and emitter, are separate entities, which means they are not covalently linked or do not form part of the same molecule.

Sometimes in this application, reference is made to certain process steps denoted by "a", "b", "c", etc. This is meant to refer to a sequence of steps wherein step a) occurs before step b) which, in turn, occurs before step c) and so forth.

In accordance with the present invention there are various ways of inducing a polymer to form polymeric nanoparticles. For example the polymer can be emulsified in a solvent which is subsequently evaporated or diffused ("emulsification followed by solvent evaporation or solvent diffusion"). Alternatively, the polymer can be dissolved and subsequently precipitated by altering, preferably increasing, the ionic strength of the solvent ("salting out"). In a further possibility, the polymer is first dissolved in an organic water-miscible solvent, such as benzyl alcohol, tetrahydrofurane or acetone and is subsequently mixed rapidly in a period $\leqq 5$ seconds, preferably $\leqq 3$ seconds, more preferably $\leqq 1$ seconds with an aqueous phase. The water-miscible organic solvent will mix with the aqueous phase, and the polymer will subsequently precipitate and form polymeric nanoparticles. This latter process is also sometimes referred to as "solvent displacement". It can optionally be followed by further drying and resuspending steps.

In other embodiments, polymeric nanoparticles in accordance with the present invention can be formed by starting from monomers. This is herein also sometimes referred to as "emulsion polymerization", wherein monomers are provided dissolved in a solvent, possibly together with a surfactant and/or a steric stabilizer, and subsequently polymerization of the monomer is initiated, leading to the formation of a polymer in the form of polymeric nanoparticles.

In preferred embodiments in accordance with the present invention, the polymer used as stabilizing agent is an amphiphilic block copolymer which preferably comprises at least one hydrophobic block and at least one hydrophilic block. In the polymeric nanoparticle, a medium for photon up-conversion is incorporated which includes the sensitizer and the emitter component and also includes a polymeric organic matrix component, the latter forming the bulk of the matrix alone or together with the hydrophobic blocks of the amphiphilic block copolymer. In some embodiments the hydrophobic part of the stabilizing agent contributes to or is the matrix as well. In some embodiments, the hydrophilic block will form a hydrophilic shell on the outside of the polymeric nanoparticle. It should be noted that, in accordance with certain embodiments of the present invention, the first component acting as sensitizer and the second component acting as emitter are separate components in the sense that they are not covalently linked or do not form part of the same molecule.

In the embodiments of the method according to the present invention, for example in embodiments involving the "solvent displacement technique", a rapid mixing of different liquid phases is necessary. This can be achieved in its simplest form by squirting one liquid phase into the other one and mixing thoroughly. Preferably such process takes place on a time scale shorter than 10 s, preferably shorter than 5 s, even more preferably shorter than is. Other more sophisticated devices are also available for the same purpose such as jet mixers, wherein the two or more liquid phases are injected under pressure from jets into a mixing chamber. Likewise there are also microfluidic devices available using hydrodynamic flow focusing where the phase containing the pre-formed polymer, preferably dissolved in a water-miscible organic solvent, is focused into a thin stream between two water streams with higher flow rates. Rapid mixing and precipitation/solvent displacement occur due to diffusion of the water-miscible solvent out of the focussed stream and diffusion of water into the focused stream.

The up-conversion nanoparticles according to the present invention do not rely on high intensity monochromatic laser light. On the contrary, even the sun and, for example, parts of the solar spectrum, such as the red or the near-infrared (NIR) region may be used as excitation source. This feature is particularly helpful in the context of biological applications, since the high intensity ultraviolet portion of the spectrum includes wavelengths that are known to produce DNA lesions and damage cells. The up-conversion efficiency is still very high even with maximum excitation intensities as low 10 mW/cm$^2$. Additionally, the ability to use infrared excitation for stimulating the up-converting nanoparticles allows the use of inexpensive IR and NIR diode lasers.

To the best of the inventors' knowledge, the nanoparticles according to the present invention also represent the first examples of photon up-conversion by all-organic active compounds in an aqueous environment. They are applicable for a wide range of biological, medical, and pharmaceutical applications. They are non-toxic and biocompatible, and the nanometer scale of the particles allows for good tissue and cell penetration. Their organic nature facilitates functionalization (via attachment of functional groups) and, thus, bioconjugation.

The emission spectrum of the up-conversion nanoparticles is spectrally rich and can be adjusted to any colour ranging from red to blue. When used as direct labels, their advantages include an improved signal-to-noise ratio due to absence of autofluorescence and reduction of light scattering, easy in vivo imaging by non-invasive and deep penetration of NIR radiation, low photobleaching, and feasibility of multiple labelling with different emissions under the same excitation.

The present invention also provides a greater versatility thanks to the possibility to combine the properties of at least two independently active compounds, by which a new system/composition is created having a variety of properties which are not shown by each component, when on its own. For example, the absorbing molecules, i.e. "sensitizer" molecules can be varied, whereby the lower energy wavelengths to be up-converted can be varied. Alternatively or in addition thereto, the emissive molecule can be varied, thereby allowing a variation of the higher energy wavelengths of the up-converted emission.

Without wishing to be bound by any theory, the principles of operation of the up-conversion process in accordance with one embodiment of a triplet-triplet annihilation assisted photon energy up-conversion system of the present invention is that after absorption of a photon in a singlet Q-band of the first component, e.g. a metallated porphyrin macrocycle (MOEP), due to an effective inter-system crossing (ISC), the long lived triplet state of the first component (sensitizer) is highly populated. This triplet state can further be considered as a reservoir of excited states for subsequent energy transfer processes. From here, two excitation pathways are possible. First, as a consequence of a triplet-triplet annihilation (TTA) process between the excited molecules of said first component themselves, one of the first component-molecules returns to the ground state and the other is excited into a higher singlet state. This is followed by an effective transfer of the first component singlet excitation to the excited singlet state of the second component, which is the emissive component, such as a blue emitter. Secondly, an additional up-conversion-channel is possible, comprising firstly a transfer of the triplet excitation of the first component directly to the triplet state of the second emissive component's molecules, followed again by effective triplet-triplet-annihilation, this time of the second component triplet states, resulting again in an excited singlet state of the second (emissive) component.

Reference is now made to the figures, wherein

Figure 1:
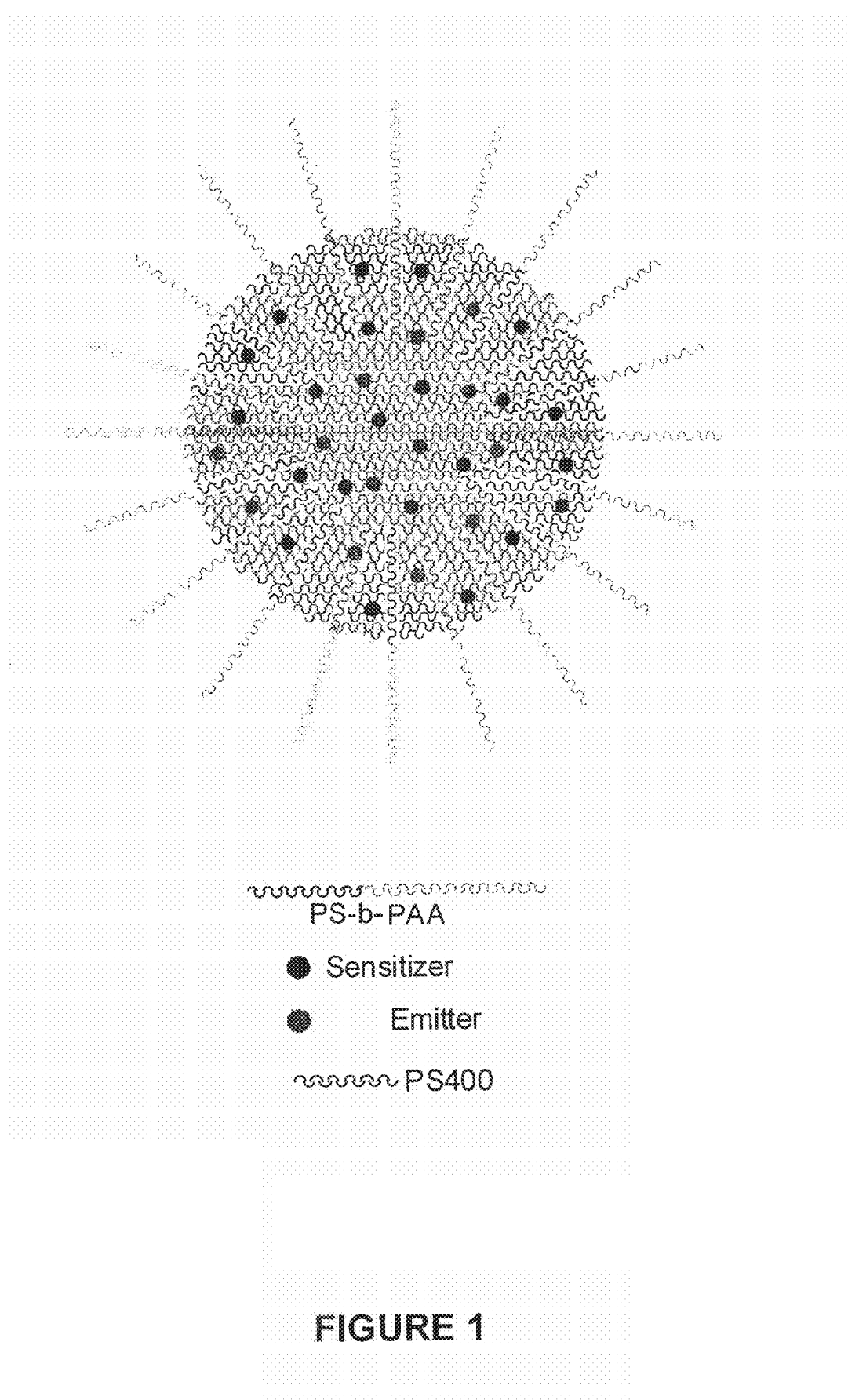
FIG. 1 is a schematic representation of the photon up-conversion nanoparticles prepared by emulsification, using an amphiphilic block copolymer (PS-b-PAA) as stabilizing agent and styrene oligomer (PS400) as polymeric organic matrix component.
Figure 2:
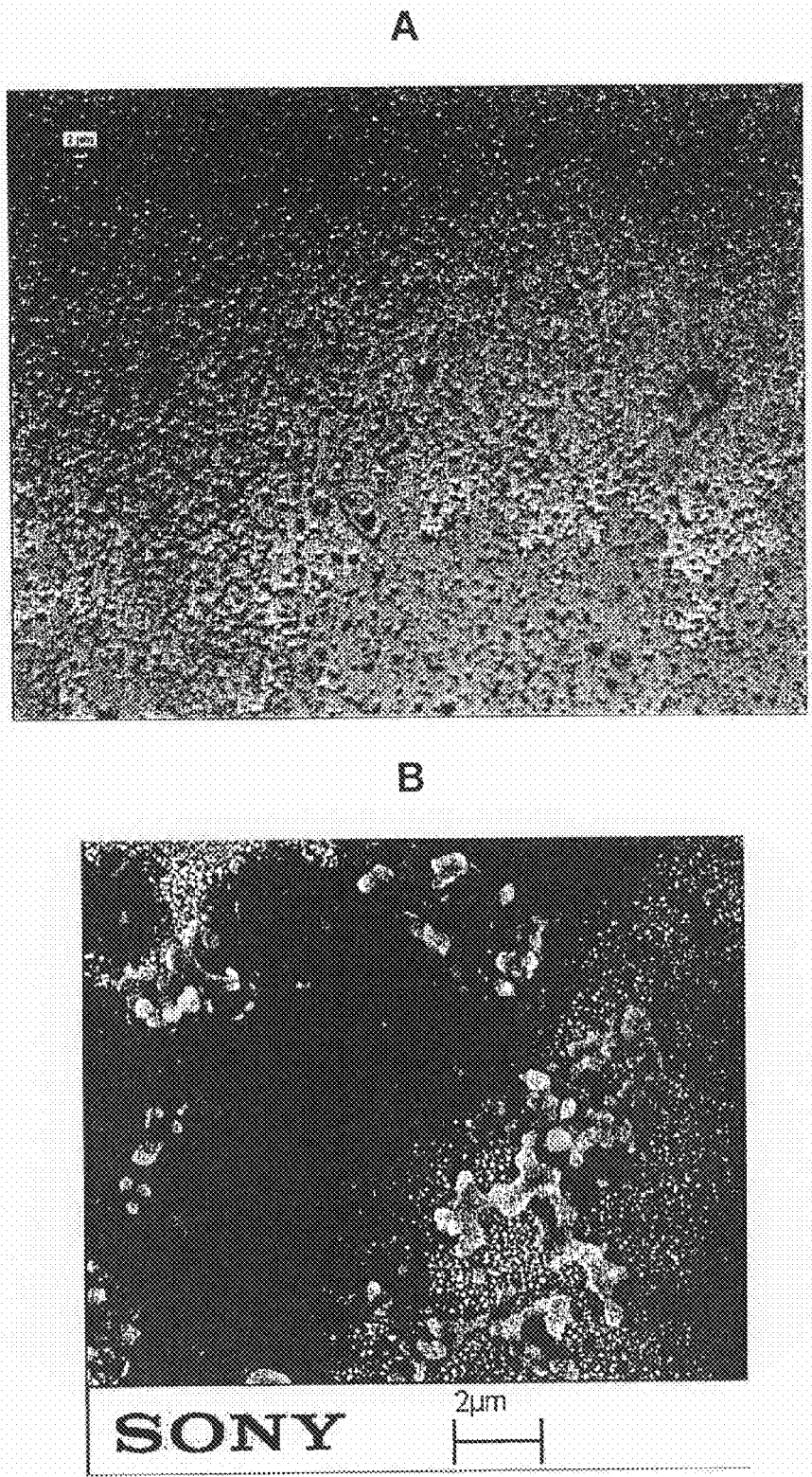
FIG. 2A is an optical photomicrograph showing up-conversion nanoparticles (UC NPs) prepared from the following mixture.
Figure 3:
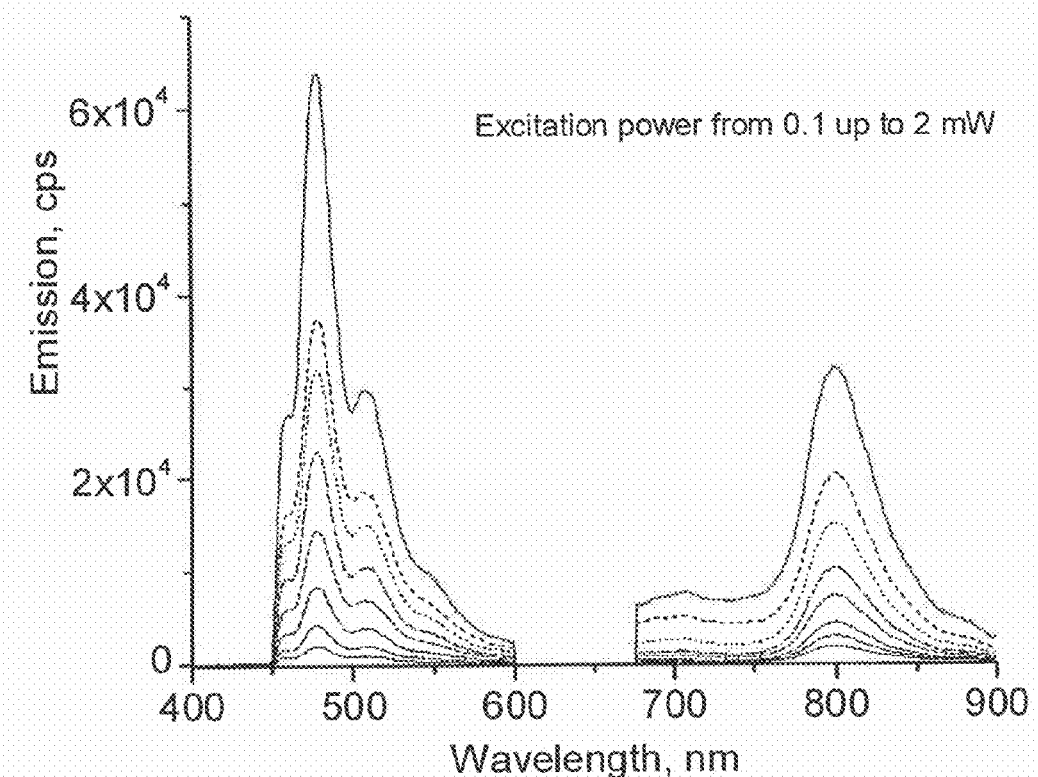
Figure 3:
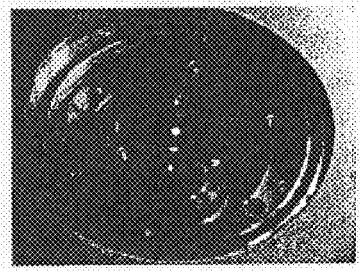
Figure 4:
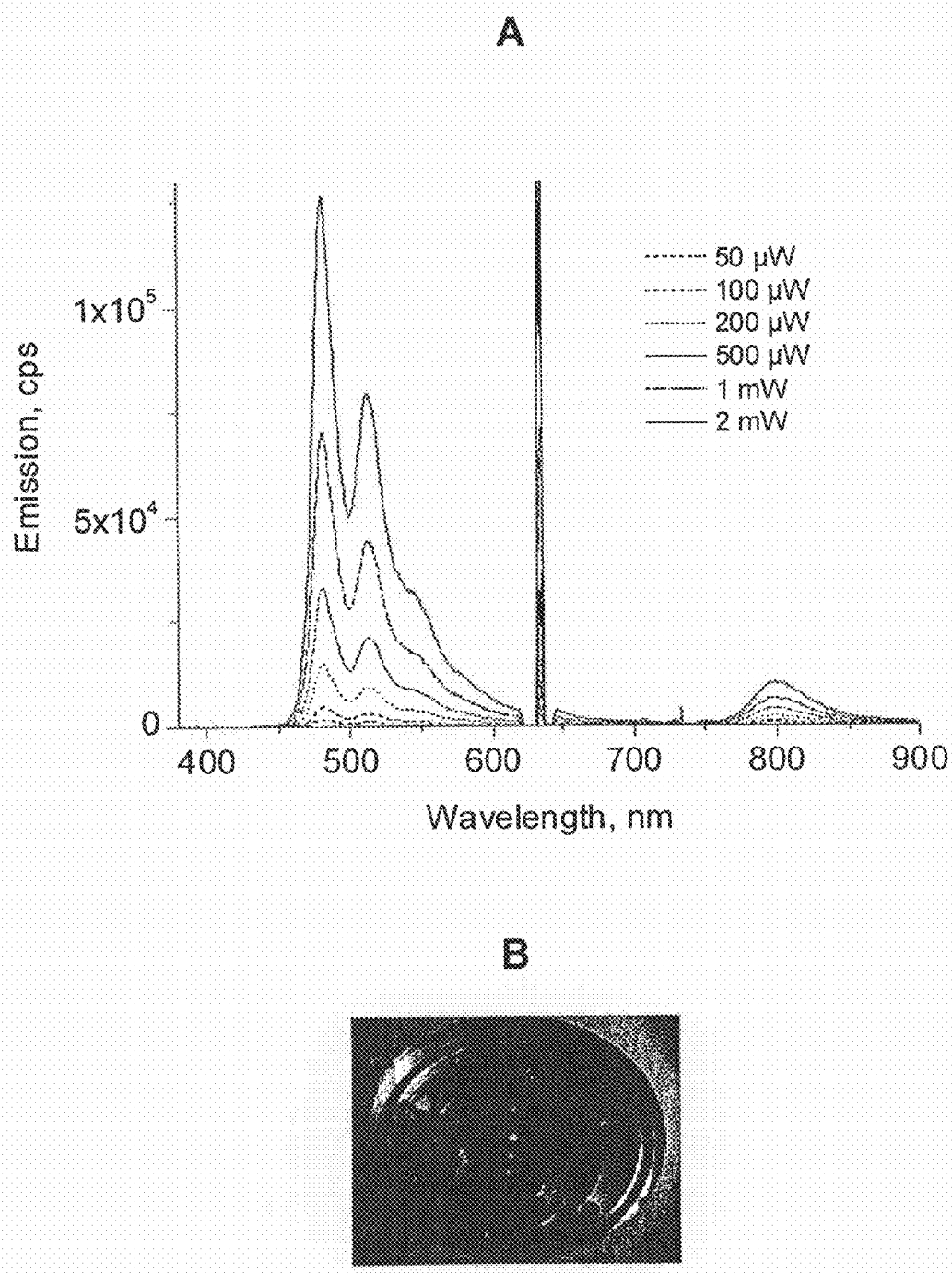
Figure 4:
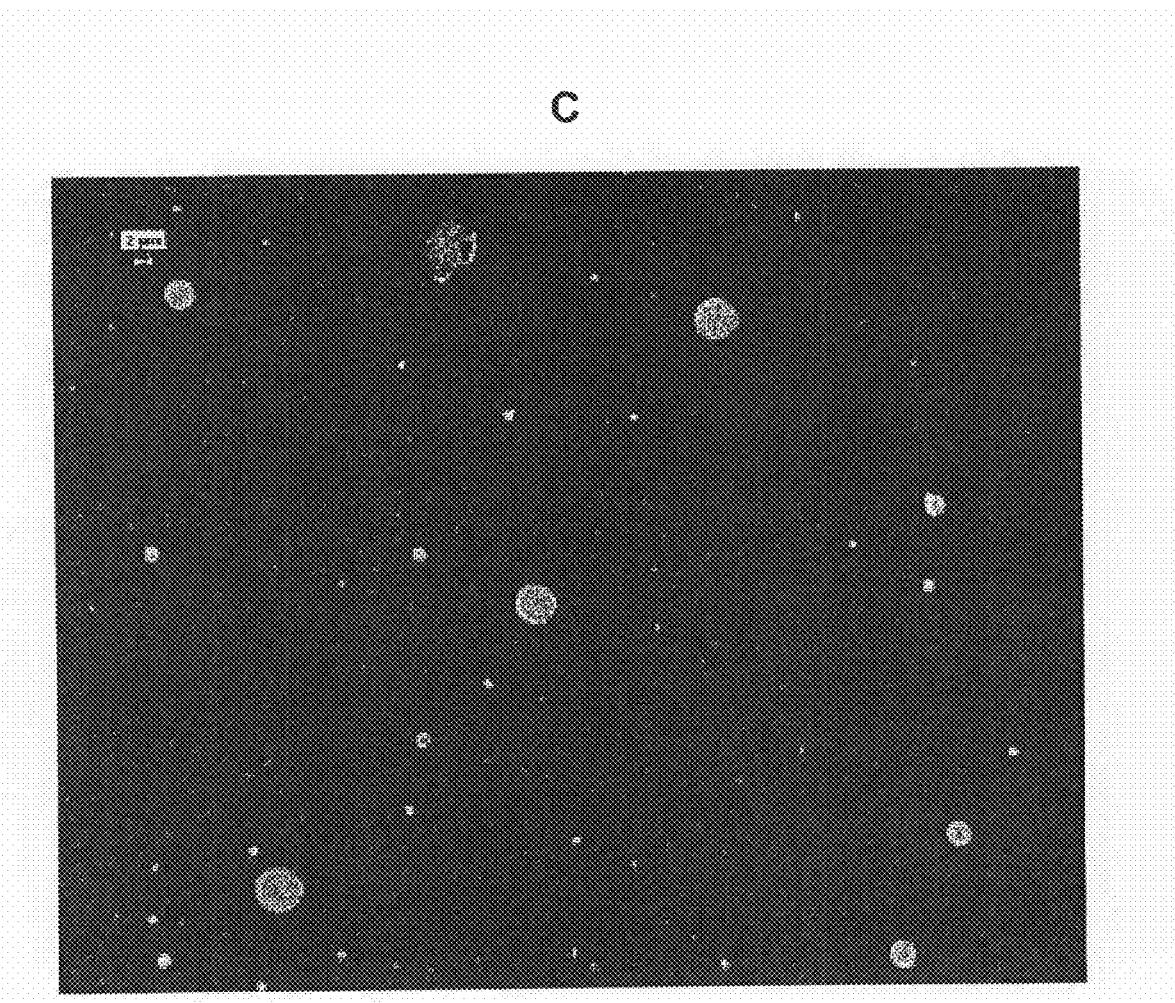
Figure 5:
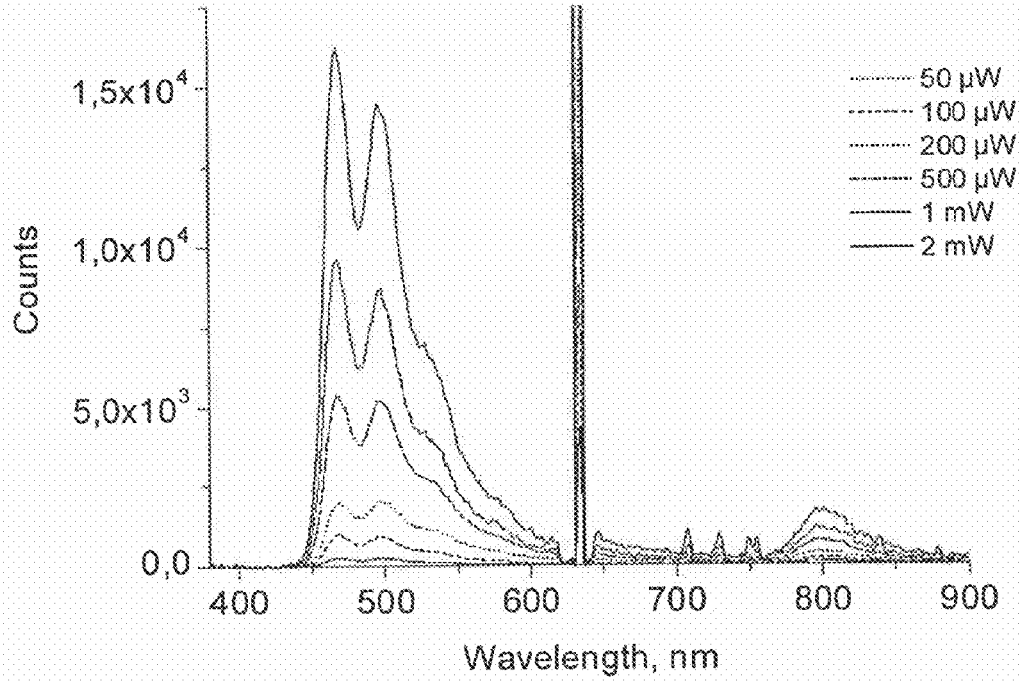
Figure 6:
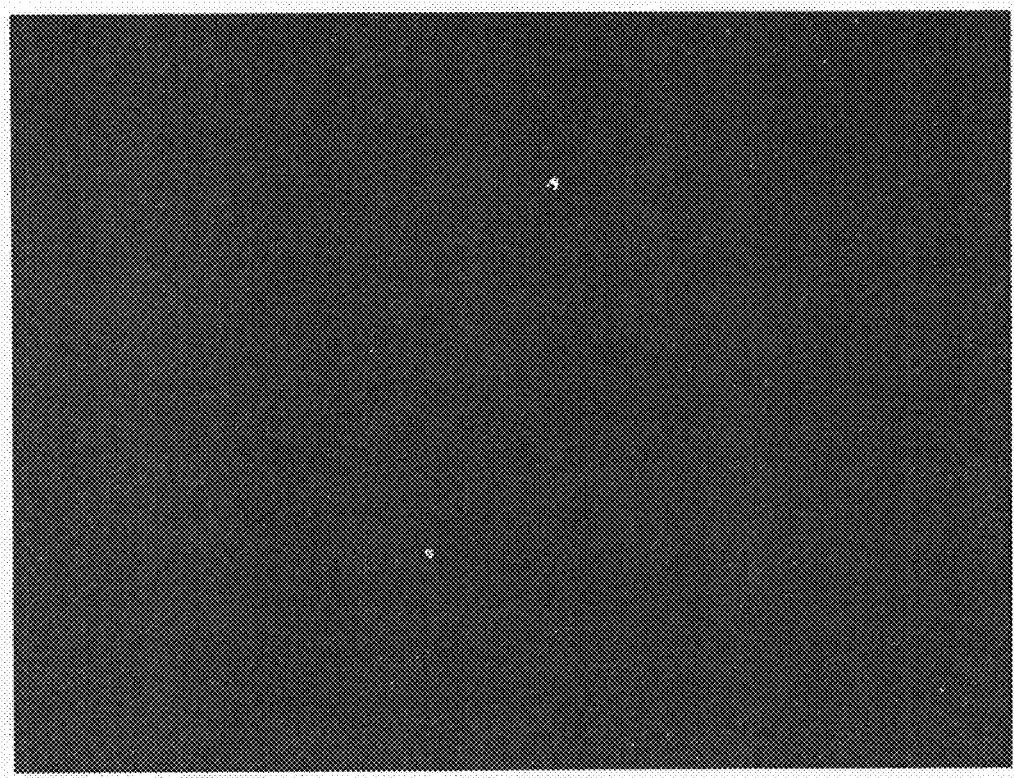
Figure 7:
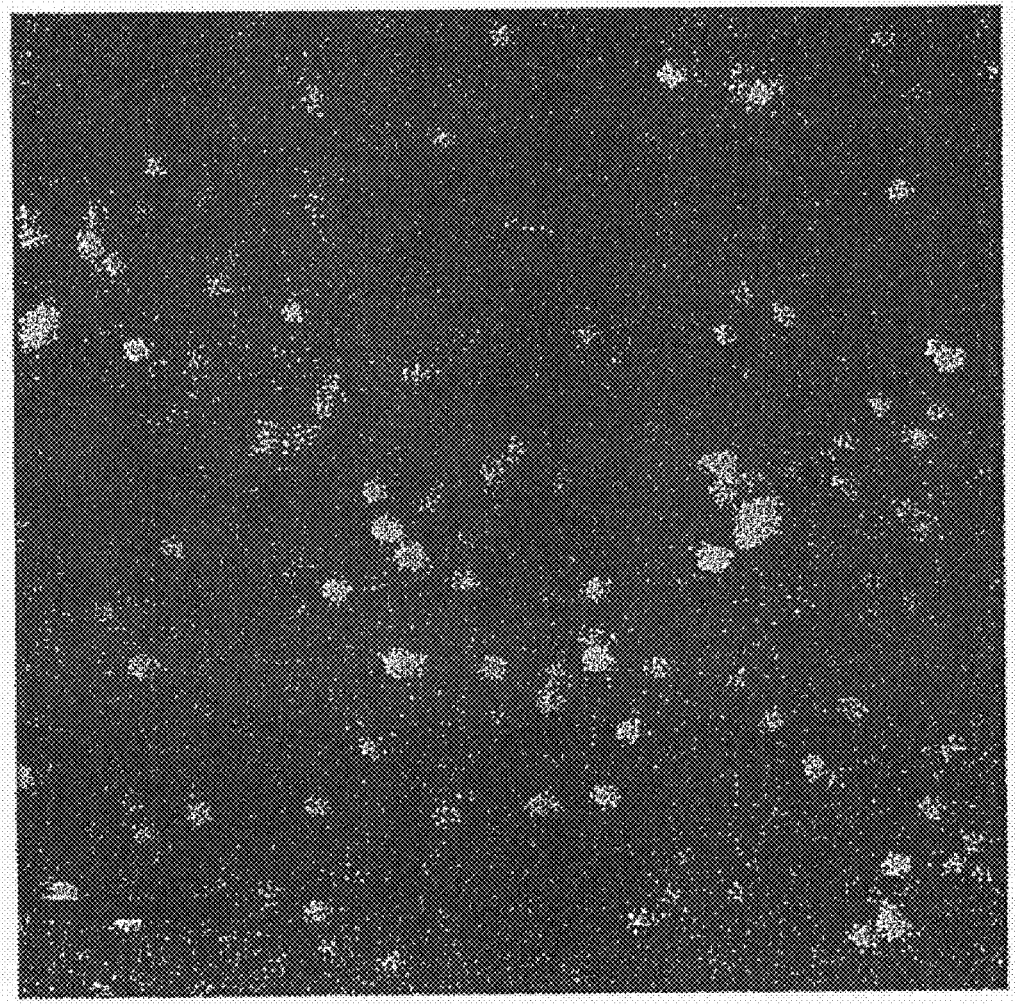

10 mg PS-b-AA
6 mg PS400 (polystyrene with a molecular weight of 400)
0.1 mg BPEA (200 µl of a 0.5 mg/ml solution in THF)
0.023 mg PdTBP (46 µl of a 0.5 mg/ml solution in THF)
9.8 ml THF;

FIG. 2B is a electron microscopy (SEM) picture of temperature-sensing nanoparticles (TS NPs) prepared from the following mixture (TS NPs only contain sensitizer molecules, preferably PdTBP or Pd Octaethylpophyrin):

10 mg PS-b-AA
6 mg PS29000 (polystyrene with a molecular weight of 29000)
0.18 mg PdTBP (180 µl of a 1 mg/ml solution in THF)
9.8 ml THF;

FIG. 3A shows the photon up-conversion spectra of UC NPs excited with 633 nm (the different curves correspond to different intensities of 632 nm excitation), prepared from the following mixture:

10 mg PS-b-AA
6 mg PS400 (polystyrene with a molecular weight of 400)
0.063 mg Perylene (126 µl of a 0.5 mg/ml solution in THF)
0.023 mg PdTBP (46 µl of a 0.5 mg/ml solution in THF)
9.8 ml THF;

FIG. 3B is a photograph of the corresponding up-conversion emission;

FIG. 4A shows the photon up-conversion spectra of UC NPs excited with 633 nm (the different curves correspond to different intensities of 632 nm excitation), prepared from the following mixture:
  10 mg PS-b-AA
  6 mg PS400 (polystyrene with a molecular weight of 400)
  0.1 mg BPEA (200 µl of a 0.5 mg/ml solution in THF)
  0.023 mg PdTBP (46 µl of a 0.5 mg/ml solution in THF)
  9.8 ml THF;

FIG. 4B is a photograph of the corresponding up-conversion emission;

FIG. 4C is a photomicrograph of the fluorescence (direct excitation with blue light ca. 400 nm) of the nanoparticles dispersed on a glass substrate;

FIG. 5 shows the photon up-conversion spectra of UC NPs excited with 633 nm (the different curves correspond to different intensities of 632 nm excitation), prepared from the following mixture:
  10 mg PS-b-AA
  6 mg PS400 (polystyrene with a molecular weight of 400)
  0.08 mg PhP (200 µl of a 0.5 mg/ml solution in THF)
  0.023 mg PdTBP (46 µl of a 0.5 mg/ml solution in THF)
  9.8 ml THF;

FIG. 6 shows a photomicrograph of the fluorescence (direct excitation with blue light ca. 400 nm) of UC NPs dispersed on a polymer film (polyvinyl alcohol—PVA). Different amounts of PVA were added to a water dispersion of the UC NPs. Films were prepared via drop-casting or spin-coating on glass substrates. The photomicrograph shows a film prepared by drop-casting (thickness ca. 50 µm). The UC NPs were prepared from the following mixture:
  10 mg PS-b-AA
  6 mg PS400 (polystyrene with a molecular weight of 400)
  0.1 mg BPEA (200 µl of a 0.5 mg/ml solution in THF)
  0.023 mg PdTBP (46 ml of a 0.5 mg/ml solution in THF)
  9.8 ml THF;

FIG. 7 shows a confocal microscope scan of nanoparticles emitting upconverted light. Excitation is done with 633 nm (continuous wave, HeNe laser, 1 mJcm$^{-2}$). Detection is only of wavelengths shorter than 532 nm (only upconverted emission is detected). Nanoparticles are in PVA drop-casted film (Nanoparticles and film preparation as described in FIG. 6).

Figure 8:
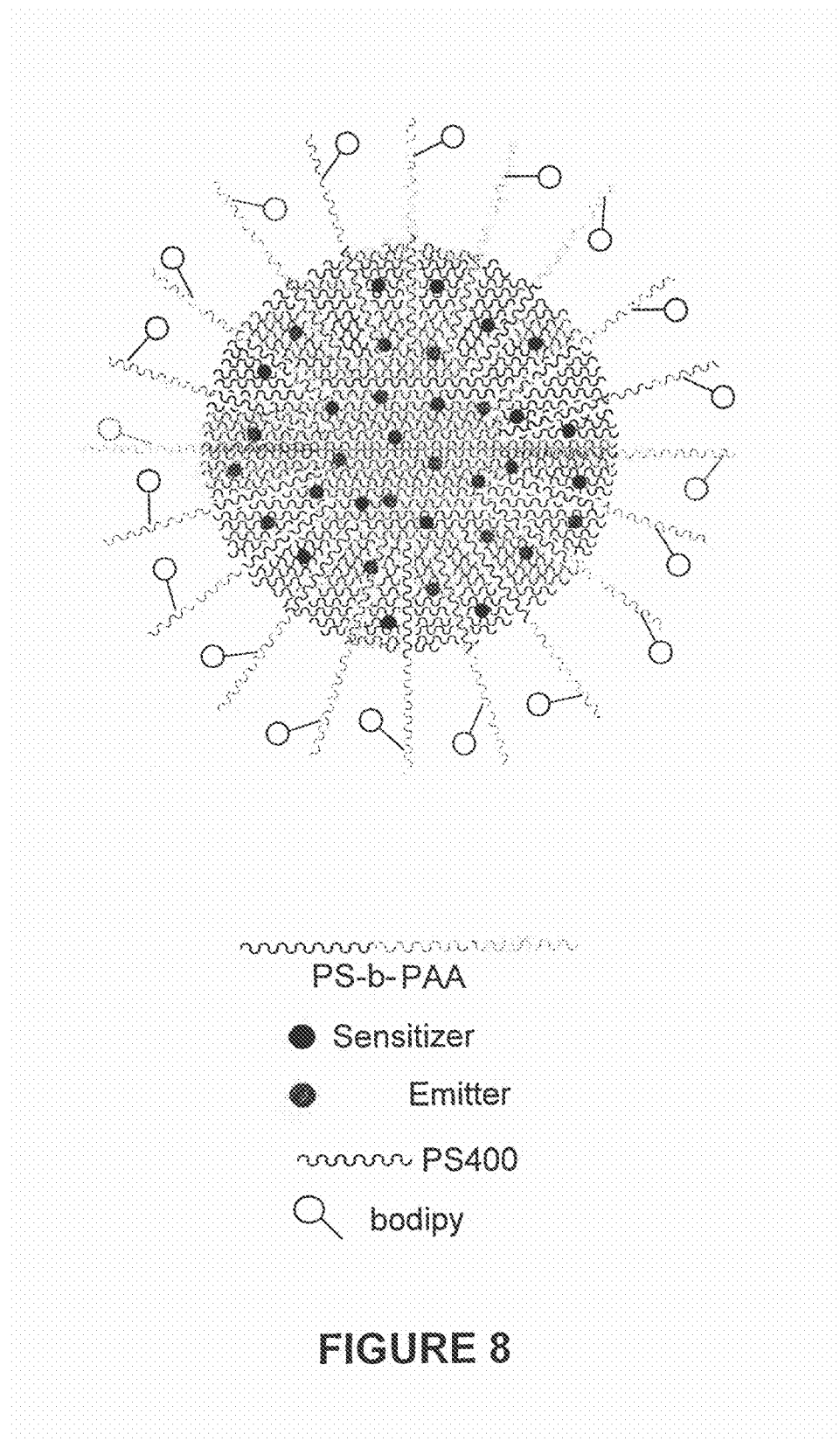
Figure 9:
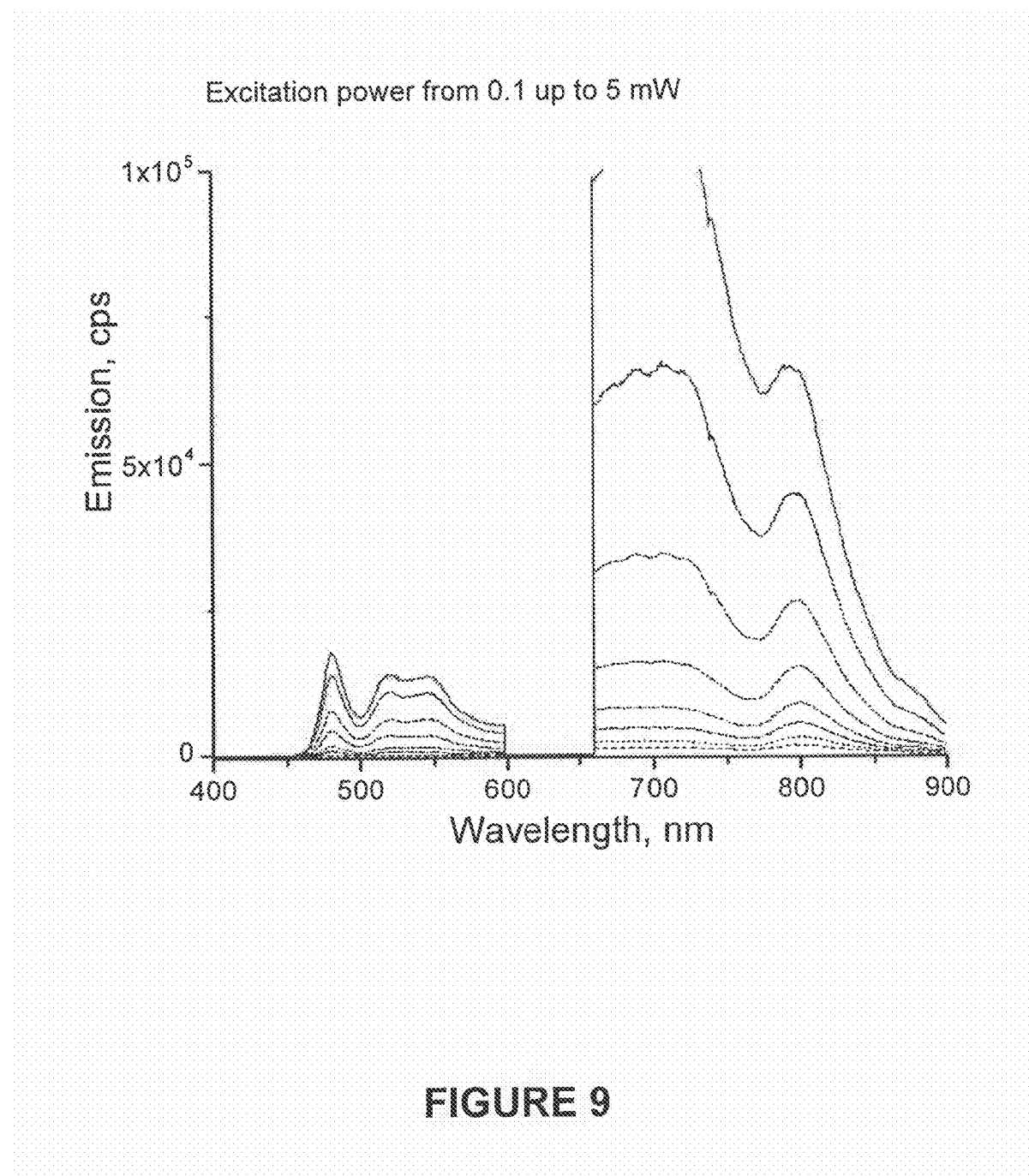

FIG. 8 is a schematic representation of the photon up-conversion nanoparticles prepared by emulsification, using an amphiphilic block copolymer (PS-b-PAA) as stabilizing agent and styrene oligomer (PS400) as polymeric organic matrix component after further labelling with bodipy (4,4-difluoro-5,7-dimethyl-4-bora-3a,4a-diaza-s-indacene-3-propionyl ethylenediamine hydrochlorid—BODIPY® FL EDA from Invitrogen);

FIG. 9 shows the photon up-conversion spectra of UC NPs excited with 633 nm (the different curves correspond to different intensities of 633 nm excitation), prepared from the following mixture:
  10 mg PS-b-AA
  6 mg PS400 (polystyrene with a molecular weight of 400)
  0.1 mg BPEA (200 µl of a 0.5 mg/ml solution in THF)
  0.023 mg PdTBP (46 µl of a 0.5 mg/ml solution in THF)
  9.8 ml THF.

Figure 10:
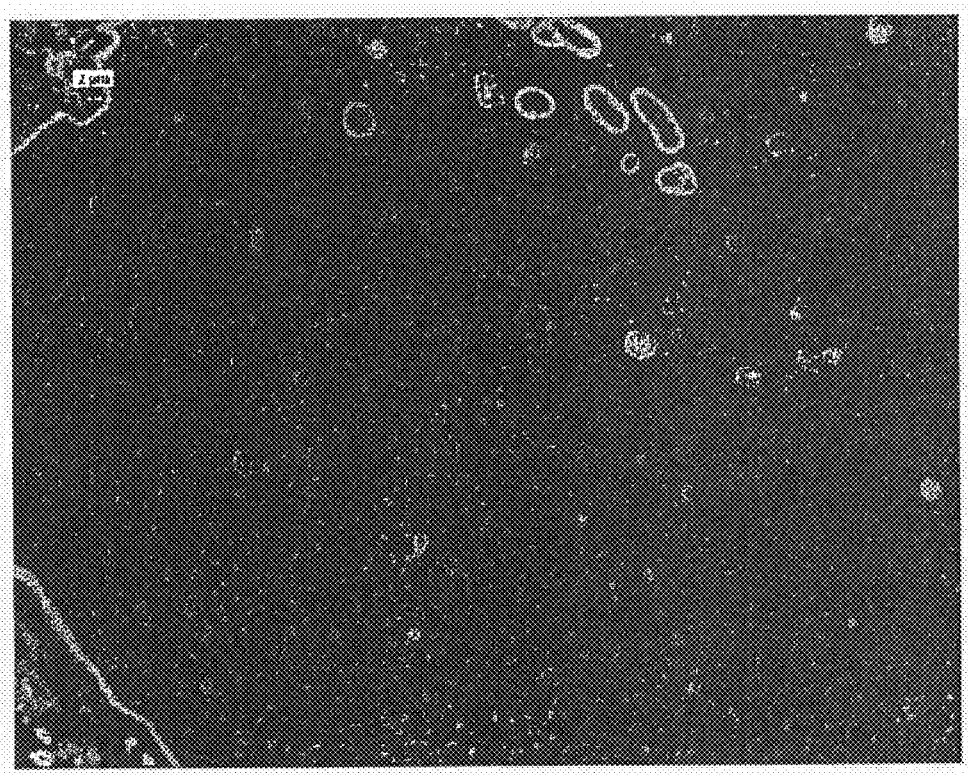
Figure 11:
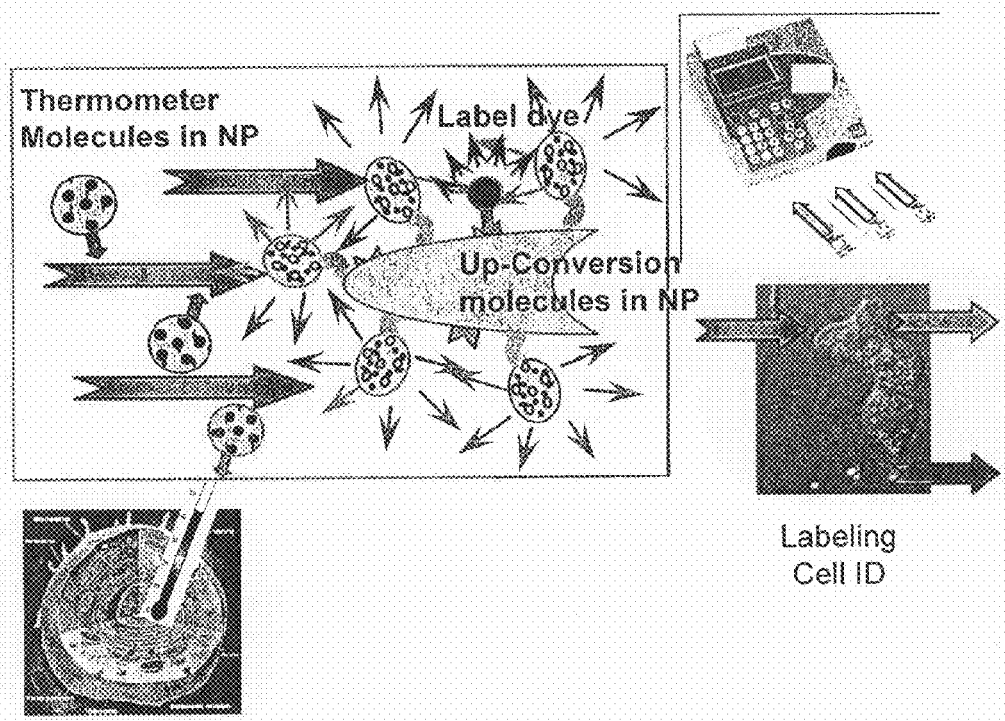
Figure 12:
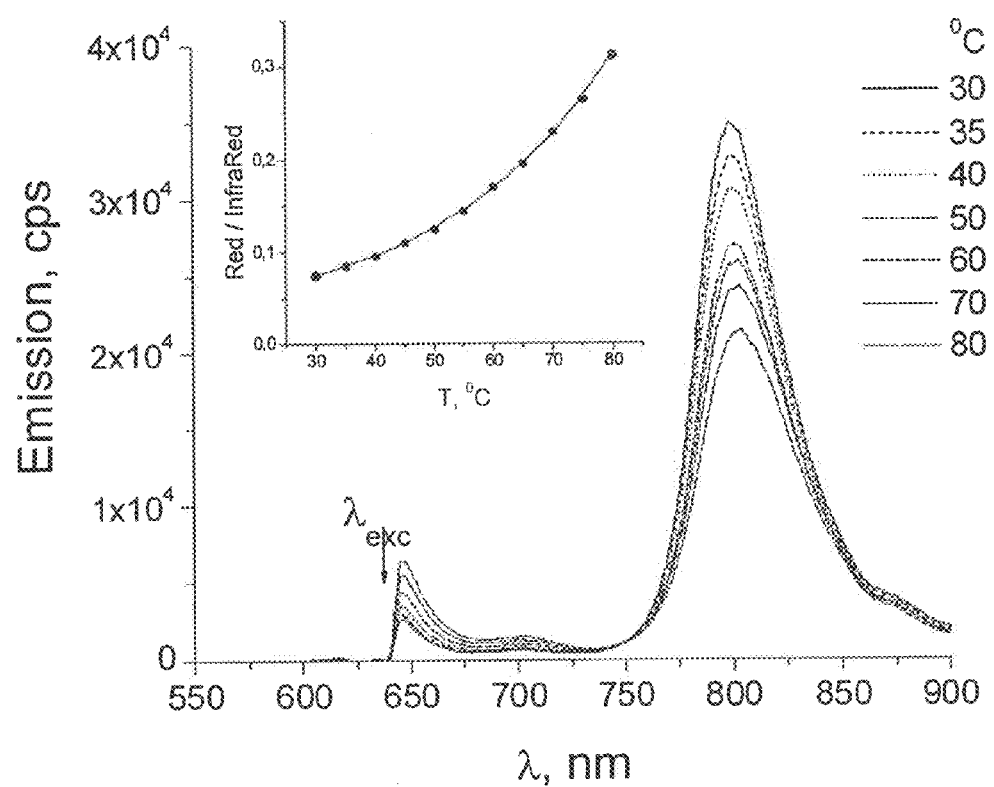

The NPs were further labelled with bodipy (see FIG. 7). The emission in the region 530 to 560 nm is the bodipy emission, excited by the upconverted emission from the NPs. As a result, the upconverted emission from the NPs is strongly decreased in comparison to NPs without further labelling (see FIG. 4A);

FIG. 10 is a photomicrograph of the fluorescence (direct excitation with blue light ca. 400 nm) of UC NPs further labelled with bodipy. The UC NPs were prepared from the following mixture:
  10 mg PS-b-AA
  6 mg PS400 (polystyrene with a molecular weight of 400)
  0.1 mg BPEA (200 µl of a 0.5 mg/ml solution in THF)
  0.023 mg PdTBP (46 µl of a 0.5 mg/ml solution in THF)
  9.8 ml THF;

FIG. 11 is a schematic representation of some possible uses of UC and TS NPs in biological applications (e.g. assays, cell labelling, temperature-sensing in cells and other biological objects);

FIG. 12 shows temperature-dependent emission spectra of NPs, as excited with 633 nm, prepared from the following mixture:
  10 mg PS-b-AA
  6 mg PS400 (polystyrene with a molecular weight of 400)
  0.023 mg PdTBP (46 µl of a 0.5 mg/ml solution in THF)
  9.8 ml THF.

Figure 13:
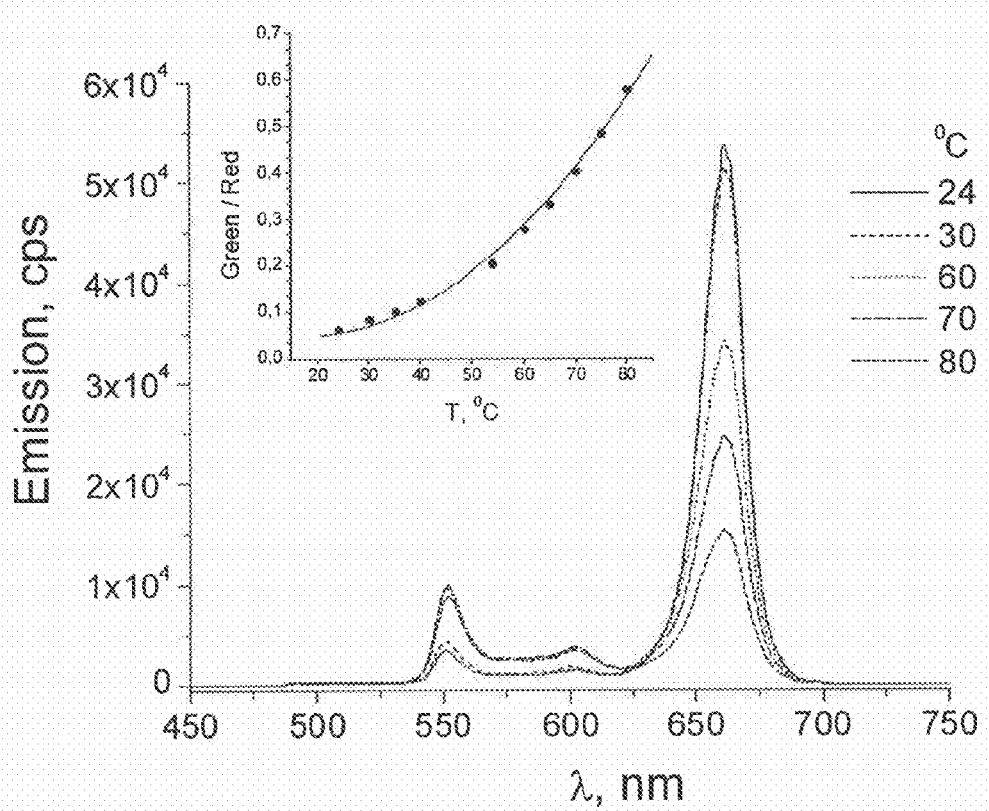

The spectra were measured using water-dispersed NPs by heating the water dispersion. The inset graph shows the dependence of the ratio (ratiometric response) of the NPs' emission at 649 and 800 nm (excitation with 633 nm; all wavelengths within the tissue window);

FIG. 13 shows temperature-dependent emission spectra of NPs, prepared from the following mixture:
  10 mg PS-b-AA
  6 mg PS29000 (polystyrene with a molecular weight of 29000)
  0.18 mg PdOEP (180 µl of a 1 mg/ml solution in THF)
  9.8 ml THF.

The spectra were measured using water-dispersed NPs by heating the water dispersion. The smaller graph shows the dependence of the ratio (ratiometric response) of the NPs' emission at 549 and 652 nm (excitation with 407 nm).

The invention is now further described by reference to the following examples, which are intended to illustrate, not to limit the scope of the invention.

Example 1

Preparation of Nanoparticles

The amphiphilic block copolymer as stabilizing agent, a polymer as polymeric organic matrix component and the at least two organic dyes ($5\times10^{-5}$ M for sensitizer, $5\times10^{-4}$ M for emitter) are dissolved in THF (tetrahydrofuran), and the resulting solution (volume: 10 ml) is stirred for 2 hours. Then, 40 ml of MilliQ water are added by pouring the 40 ml in one go (within 1 s). Other possibilities for mixing the solution with an aqueous phase have been outlined further above. The solution is stirred overnight (or for up 48 hours) and filtered under vacuum through Whatman #1 filter paper. Afterwards, first THF and then the water are removed using a vacuum rotation dryer, and the residuum is dried on the vacuum line for another 2 hours. Subsequently, 40 ml of MilliQ water are added and the solution is stirred overnight, followed by removal of the water and drying as described above. Finally, the residuum is dissolved in 10 ml MilliQ water (resulting in a homogenous dispersion of the nanoparticles) and stored at 4° C. until filtration with HiTrap filters prior to use of the nanoparticles.

Nanoparticles
1. Perylene/PdTBP—blue emission
2. PhP/PdTBP—blue emission but red-shifted in comparison to 1.
3. BPEA/PdTBP—green emission
4. Rubrene/PdOPhPc—yellow emission
5. Rubrene/PdTBP—yellow emission Nanoparticle 1
Amphiphilic block copolymer: 10 mg PS-b-PAA (polystyrene-block-polyacrylic acid)
Polymer: 6 mg PS400 (polystyrene with a molecular weight of 400)
Emitter: 0.063 mg Perylene (dibenz[de,kl]anthracene) (126 μl of a 0.5 mg/ml solution in THF)
Sensitizer: 0.023 mg PdTBP (meso-tetraphenyl-tetrabenzoporphyrin palladium) (46 μl of a 0.5 mg/ml solution in THF)
(+9.8 ml THF)

Nanoparticle 2
Amphiphilic block copolymer: 10 mg PS-b-PAA
Polymer: 6 mg PS400
Emitter: 0.08 mg PhP (3-phenyl-perylene) (164 μl of a 0.5 mg/ml solution in THF)
Sensitizer: 0.023 mg PdTBP (46 μl of a 0.5 mg/ml solution in THF)
(+9.8 ml THF)

Nanoparticle 3
Amphiphilic block copolymer: 10 mg PS-b-PAA
Polymer: 6 mg PS400
Emitter: 0.1 mg BPEA (9,10-bis(phenylethynyl)anthracene) (200 μl of a 0.5 mg/ml solution in THF)
Sensitizer: 0.023 mg PdTBP (46 μl of a 0.5 mg/ml solution in THF)
(+9.8 ml THF)

Nanoparticle 4
Amphiphilic block copolymer: 10 mg PS-b-PAA
Polymer: 6 mg PS400
Emitter 0.12 mg Rubrene (240 μl of a 0.5 mg/ml solution in THF)
Sensitizer: 0.022 mg PdOPhPc (Palladium(II) 1,8,15,22-Tetraphenoxy-phthalocyanine) (44 μl of a 0.5 mg/ml solution in THF)
(+9.8 ml THF)

Nanoparticle 5
Amphiphilic block copolymer: 10 mg PS-b-PAA
Polymer: 6 mg PS400
Emitter: 0.12 mg Rubrene (240 μl of a 0.5 mg/ml solution in THF)
Sensitizer: 0.023 mg PdTBP (46 μl of a 0.5 mg/ml solution in THF)
(+9.8 ml THF)

Nanoparticle 6 (FIG. 12)
Amphiphilic block copolymer: 10 mg PS-b-PAA
Polymer: 6 mg PS29000 (Mw is 29 000)
Sensitizer: 0.18 mg PdTBP (180 μl of a 1 mg/ml solution in THF)
(+9.8 ml THF)

Nanoparticle 7 (FIG. 2B, FIG. 13)
Amphiphilic block copolymer: 10 mg PS-b-PAA
Polymer: 6 mg PS29000 (Mw is 29 000)
Sensitizer: 0.18 mg PdOEP (octaethyl-porphyrin palladium) (180 μl of a 1 mg/ml solution in THF)
(+9.8 ml THF)

The PS-b-PAA copolymer used for nanoparticles 1-4 has the general structure

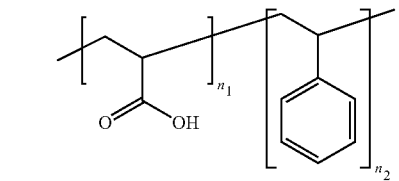

with $n_1$=6000 and $n_2$=1800.

Example 2

Up-Conversion Emission of the Nanoparticles

Nanoparticles (NPs) according to the present invention were dispersed in water and excited with light of different intensities at 633 nm. FIGS. 3A, 4A and 5 show emission spectra of nanoparticles with perylene as emitter (=Nanoparticle 1, Example 1), with BPEA as emitter (=Nanoparticle 3, Example 1) and with PhP as emitter (Nanoparticle 2, Example 1), respectively. In all three cases, the spectra show highly efficient up-conversion (with a peak at ~480 nm, =blue light) even with excitation intensities as low 5-10 mW/cm².

Example 3

Attachment and UC Excitation of Additional Dyes

The structure of the nanoparticles according to the present invention allows the attachment of (an) additional label(s) to the hydrophilic parts of the amphiphilic block copolymer. Such additional label(s) could then be excited by the emission of the up-converting nanoparticle. This principle was tested using nanoparticles according to the present invention carrying the organic dye bodipy (Invitrogen) (see FIGS. 7-9).

Bodipy was coupled to the hydrophilic part of the PS-b-PAA copolymer as follows:

Stock Solutions:
EDC: 4.4 mg of 1-ethyl-3-(3-dimethylaminopropyl)-carbodiimide-hydrochlorid in 5 ml MilliQ water
Bodipy (BP): 1.53 mg in 0.9 ml MilliQ water
NP stock solution (see Example 1)

Procedure:
0.75 ml of the NP stock solution were mixed with 0.09 ml EDC solution and stirred for 5 min. Subsequently, 0.09 ml of BP solution and 0.57 ml MilliQ water were added. The resulting 1.5 ml solution was stirred for 2 hours and then filtered using a HiTrap filter—approximately every $50^{th}$ COOH group was activated and coupled to BP.

Bodipy—which absorbs light at ~480 nm (blue) and emits light at ~530 nm (green) —is excited by the emission of the up-conversion nanoparticles according to the present invention excited at 632 nm.

Example 4

Temperature-Sensing Nanoparticles (TS NPs)

FIGS. 2B, 12 and 13 show examples of temperature-sensing nanoparticles (TS NPs). TS NPs do not contain a sensitizer/emitter pair, but only sensitizer molecules, preferably PdTBP or Pd Octaethylpophyrin.

The features of the present invention disclosed in the specification, the claims and/or in the figures may, both separately and in any combination thereof, be material for realizing the invention in various forms thereof.

The invention claimed is:

1. A polymeric nanoparticle suitable for a biological application, comprising
a medium for photon up-conversion and a stabilizing agent, said medium comprising at least two components and a polymeric organic matrix component, said polymeric organic matrix component forming a polymeric matrix in which polymeric matrix said at least two components are distributed, wherein a first component of said at least two components is capable of absorbing light at a first wavelength region $\lambda_1$, which first component acts as a sensitizer in said medium, and wherein a second component of said at least two components is capable of emitting light at a second wavelength region $\lambda_2$, which second component acts as an emissive component in said medium, wherein $\lambda_2 \leq \lambda_1$, and wherein, upon absorption of light by said first component at said first wavelength region $\lambda_1$, said emissive component emits light at said second wavelength region $\lambda_2$, wherein said first component and said second component are organic compounds,
wherein said stabilizing agent is a polymer selected from the group consisting of hydrophilic polymers and amphiphilic polymers, said amphiphilic polymers having a hydrophobic part and a hydrophilic part, wherein said hydrophobic part also forms part of said polymeric matrix,
wherein said amphiphilic polymer is selected from the group consisting of amphiphilic copolymers, hydrophobic polymers with a covalently attached hydrophilic part, hydrophilic polymers with a covalently attached hydrophobic part, and polyelectrolytes having a hydrophobic part,
wherein the polymeric organic matrix comprises a hydrophobic polymer selected from the group consisting of polystyrenes, styrene-butadiene copolymers, polystyrene-based elastomers, polyethylenes, polypropylenes, polytetrafluoroethylenes, extended polymethylsiloxane, polyphenylmethylsiloxanes, modified polysiloxanes, polyethers, polyurethanes, polyether-urethanes, polyethylene terephthalates, and polysulphones,
wherein the first component is an organic dye having a populated triplet or mixed triplet-singlet state, a two-photon absorbing dye, an optical limiting component, or a carbon nanotube,
wherein the second component is an organic dye having fluorescence emission of from 360 to 750 nm, and
wherein said biological application is labeling cells, detection of cells, biological (macro-) molecules or other analytes, fluorescence microscopy, (flow) cytometry, fluorescence-activated cell sorting (FACS), fluorescence resonance energy transfer (FRET), immunohistochemistry, clinical immunoassay, fluorescence-quenching-based enzyme-activity assay, high-throughput screening, molecular diagnostic, sensing of temperature, sensing of pressure, sensing of oxygen, sensing of other substances that influence the up-conversion process in cells and tissues, or singlet oxygen generation.

2. The polymeric nanoparticle according to claim 1, wherein said stabilizing agent is an amphiphilic copolymer, selected from the group consisting of an amphiphilic block, graft, random and an alternating copolymer copolymers.

3. The polymeric nanoparticle according to claim 2, wherein said stabilizing agent is an amphiphilic block copolymer or an amphiphilic graft copolymer.

4. The polymeric nanoparticle according to claim 2, wherein said amphiphilic copolymer is an amphiphilic block copolymer comprising at least one hydrophobic block and at least one hydrophilic block.

5. The polymeric nanoparticle according to claim 4, wherein said at least one hydrophobic block forms part of said polymeric matrix, and wherein said at least one hydrophilic block forms a hydrophilic shell surrounding said matrix.

6. The polymeric nanoparticle according to claim 4, wherein said hydrophilic polymer or said at least one hydrophilic block of said amphiphilic copolymer is polyethylene glycols, polyethylene oxides, polyacrylamides, polyacrylic acids or their related polymers or copolymers, acrylates, maleic anhydride copolymers, methacrylate, ethacrylate or related polymers, amine-functional polymers, ethers, styrenes, vinyl acids, or vinyl alcohols, copolymers or combinations thereof.

7. The polymeric nanoparticle according to claim 4, wherein said at least one hydrophobic block of said amphiphilic block copolymer is polystyrenes, styrene copolymers, styrene-butadiene copolymers, polystyrene-based elastomers, polyethylenes, polypropylenes, polytetrafluoroethylenes, extended polytetrafluoroethylenes, polyacrylates, polymethylmetacrylates, ethylene-co-vinyl acetates, polysiloxanes, their copolymers as well as substituted or modified polysiloxanes, polyethers, polyurethanes, polyether-urethanes, polyethylene terephthalates, or polysulphones.

8. The polymeric nanoparticle according to claim 4, wherein said at least one hydrophilic block of said amphiphilic block copolymer carries a functional group allowing bioconjugation.

9. The polymeric nanoparticle according to claim 8, wherein said functional group is —COOH (carboxylate), —SH (thiol), —NH$_2$, —NHS, alkynyl groups, —N$_3$, aldehyde, ketone, biotin group, or a group having the formula

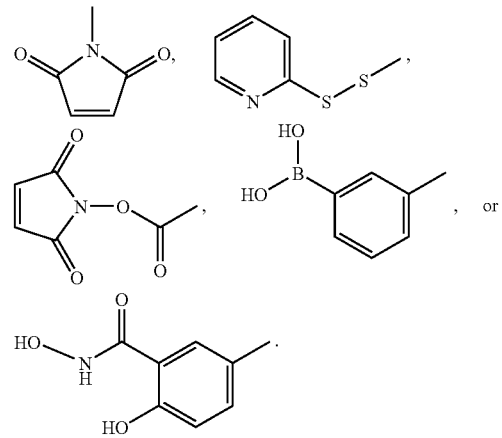

10. The polymeric nanoparticle according to claim 4, wherein said amphiphilic block copolymer has a general formula is selected from the group consisting of

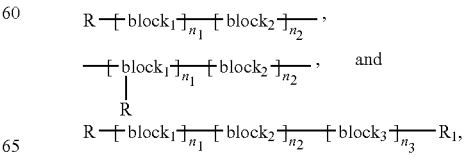

wherein block₁ and block₃ are hydrophilic,
block₂ is hydrophobic,
$n_1$, $n_2$, and $n_3$ are integer numbers from 2 to 20000, and
R and $R_1$ are functional group is —COOH (carboxylate), —SH (thiol), —NH₂, —NHS, alkynyl groups, —N₃, aldehyde, ketone, biotin group, or a group having the formula

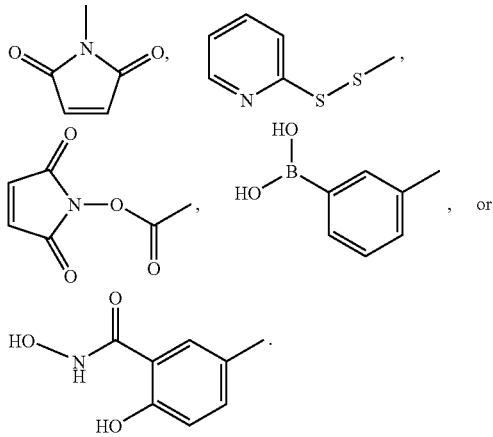

11. The polymeric nanoparticles according to claim 1, wherein said biological (macro-) molecules or other analytes are nucleic acids/(poly-)nucleotides, (poly-) peptides/proteins, carbohydrates, lipids, glycoproteins, lipoproteins, viral and/or bacterial antigens, or pharmaceuticals.

12. The polymeric nanoparticle according to claim 1, wherein the first component is selected from the group consisting of porphyrins, extended porphyrins, texaphyrins, sapphyrins, orangerins, substituted porphyrins and porphyrins containing one or more metals selected from the group consisting of Li, Mg, Al, Ti, V, Mn, Fe, Co, Ni, Cu, Zn, Ga, Ru, Pd, Ag, Re, Os, Ir, Pt, Pb, and U.

13. The polymeric nanoparticle according to claim 1, wherein the second component is selected from the group consisting of anthracenes, tetracenes, pentacenes, perylenes, substituted anthracenes, tetracenes, pentacenes, perylenes, phenyl (bi-, tri-phenyl)-bridged anthracenes, tetracenes, pentacenes, perylenes, fluorenes, thiophenes, polyfluorenes and oligofluorenes, polyparaphenylenes, including polyparaphenylene vinylene, and polyphenyleneethinylenes.

14. The polymeric nanoparticle according to clam 1, wherein the first component is PdTBP (meso-tetraphenyl-tetrabenzoporphyrin palladium) or PdOPhPc (palladium(II) 1,8,15,22-tetraphenoxy-phthalocyanine), and the second component is Perylene (dibenz[de,kl]anthracene), PhP (3-phenyl-perylene), BPEA (9,10-bis(phenylethynyl)anthracene) and Rubrene (5,6,11,12-tetraphenylnaphthacene).

* * * * *